(12) United States Patent
Ramos et al.

(10) Patent No.: US 7,132,543 B2
(45) Date of Patent: Nov. 7, 2006

(54) PARA-PHENYLENEDIAMINE DERIVATIVES CONTAINING A DISUBSTITUTED PYRROLIDINYL GROUP BEARING A CATIONIC RADICAL, AND USE OF THE SAME FOR DYEING KERATIN FIBERS

(75) Inventors: Laure Ramos, Bourg Lareine (FR); Stéphane Sabelle, Paris (FR)

(73) Assignee: L'Oreal S.A., Paris (FR)

( * ) Notice: Subject to any disclaimer, the term of this patent is extended or adjusted under 35 U.S.C. 154(b) by 313 days.

(21) Appl. No.: 10/810,814

(22) Filed: Mar. 29, 2004

(65) Prior Publication Data
US 2004/0248961 A1 Dec. 9, 2004

Related U.S. Application Data

(60) Provisional application No. 60/469,013, filed on May 9, 2003.

(30) Foreign Application Priority Data
Mar. 28, 2003 (FR) .................................. 03 03873

(51) Int. Cl.
*A61Q 5/10* (2006.01)
*C07D 207/09* (2006.01)
*C07D 207/14* (2006.01)
*C07D 401/04* (2006.01)
*C07D 401/06* (2006.01)
*C07D 403/04* (2006.01)
*C07D 403/14* (2006.01)

(52) U.S. Cl. ................ 546/256; 546/276.4; 546/278.4; 546/279.1; 548/313.1; 548/314.7; 548/518; 548/537; 548/557; 548/556; 8/405; 8/406; 8/409

(58) Field of Classification Search ................ 546/256, 546/276.4, 278.4, 279.1; 548/313.1, 314.7, 548/518, 537, 557, 566; 8/405, 406, 409
See application file for complete search history.

(56) References Cited

U.S. PATENT DOCUMENTS

| RE30,199 E | 1/1980 | Rose et al. |
|---|---|---|
| 4,823,985 A | 4/1989 | Grollier et al. |
| 5,061,289 A | 10/1991 | Clausen et al. |
| 5,380,340 A | 1/1995 | Nunhoeffer et al. |
| 5,534,267 A | 7/1996 | Nunhoeffer et al. |
| 5,663,366 A | 9/1997 | Nunhoeffer et al. |
| 5,766,576 A | 6/1998 | Lowe et al. |
| 5,851,237 A | 12/1998 | Anderson et al. |
| 5,993,491 A | 11/1999 | Lim et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,461,391 B1 * | 10/2002 | Lim et al. .................. 8/405 |
| 6,521,761 B1 * | 2/2003 | Lim et al. .................. 548/557 |
| 6,613,313 B1 | 9/2003 | Kimura |
| 6,645,258 B1 | 11/2003 | Vidal et al. |
| 6,730,789 B1 | 5/2004 | Birault et al. |
| 6,946,005 B1 * | 9/2005 | Sabelle et al. .................. 8/405 |
| 2002/0050013 A1 | 5/2002 | Vidal et al. |
| 2002/0197223 A1 | 12/2002 | Kimura |
| 2003/0019051 A9 | 1/2003 | Vidal et al. |

FOREIGN PATENT DOCUMENTS

| DE | 2359399 | 6/1975 |
|---|---|---|
| DE | 3843892 | 6/1990 |
| DE | 4133957 | 4/1993 |
| DE | 19543988 | 5/1997 |
| EP | 0 770 375 | 5/1997 |
| FR | 2586913 | 3/1987 |
| FR | 2733749 | 11/1996 |
| FR | 2801308 | 5/2001 |
| FR | 2 817 472 | 6/2002 |
| FR | 2817478 | 6/2002 |
| GB | 1026978 | 4/1966 |
| GB | 1153196 | 5/1969 |
| JP | 63-169571 | 7/1988 |
| JP | 11-158048 | 6/1999 |
| WO | WO 94/08969 | 4/1994 |
| WO | WO 94/08970 | 4/1994 |
| WO | WO 96/15765 | 5/1996 |
| WO | WO 99/03819 | 1/1999 |
| WO | WO 99/03836 | 1/1999 |
| WO | WO 02/45675 | 6/2002 |

OTHER PUBLICATIONS

English language Derwent Abstract of FR 2 817 472, Jun. 7, 2002.

* cited by examiner

*Primary Examiner*—Fiona T. Powers
(74) *Attorney, Agent, or Firm*—Finnegan, Henderson, Farabow, Garrett & Dunner L.L.P.

(57) ABSTRACT

The present disclosure relates to a novel a para-phenylenediamine derivative substituted with a pyrrolidinyl group of formula (I) and the addition salts thereof. The present disclosure also relates to a dyeing composition for keratin fibers comprising the paraphenylene derivative as at least one oxidation base, and to a process for dyeing keratin fibers and a multi-compartment kit using the claimed dye composition. Such a composition makes it possible to obtain a chromatic, powerful, unselective and fast coloration of keratin fibers.

34 Claims, No Drawings

PARA-PHENYLENEDIAMINE DERIVATIVES CONTAINING A DISUBSTITUTED PYRROLIDINYL GROUP BEARING A CATIONIC RADICAL, AND USE OF THE SAME FOR DYEING KERATIN FIBERS

This application claims benefit of U.S. Provisional Application No. 60/469,013, filed May 9, 2003.

Disclosed herein is a novel compound of formula (I), wherein this compound is a para-phenylenediamine derivative substituted with a pyrrolidinyl group bearing a cationic radical, and the addition salts thereof. The present disclosure also relates to a composition for dyeing keratin fibers comprising the compound of formula (I) as an oxidation base, a process for dyeing keratin fibers, and a multicompartment kit using the claimed dye composition.

It is known practice to dye keratin fibers, for example, human hair, with dye compositions containing oxidation dye precursors (also known as oxidation bases), such as, for example, ortho- or para-phenylenediamines, ortho- or para-aminophenols, heterocyclic compounds such as diaminopyrazole derivatives, pyrazolo[1,5-a]pyrimidine derivatives, pyrimidine derivatives, pyridine derivatives, 5,6-dihydroxyindole derivatives and 5,6-dihydroxyindoline derivatives. Oxidation dye precursors, or oxidation bases, are colorless or weakly colored compounds that, when combined with oxidizing products, can give rise to colored compounds and dyes by a process of oxidative condensation.

It is also known that the shades obtained with these oxidation bases may be varied by combining them with couplers or coloration modifiers, the latter being chosen, for example, from aromatic meta-diamines, meta-aminophenols, meta-hydroxyphenols and certain heterocyclic compounds such as, for example, pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives, and indole derivatives.

The variety of molecules used as oxidation bases and couplers allows a wide range of colors to be obtained.

It is desirable for the "permanent" coloration obtained by means of these oxidation dyes to satisfy a certain number of requirements. For example, such a coloration typically has at least one of the following properties: no toxicological drawbacks, allows shades to be obtained in the desired intensity, and shows good resistance to external agents, such as light, bad weather, washing, permanent-waving, perspiration, and rubbing.

Other properties that may be possessed by such dyes include: allowing white hairs to be covered and being as unselective as possible, i.e., producing the smallest possible color differences along the same length of keratin fiber, which may be differently sensitized between its end and its root. Further properties that may be possessed include: showing good chemical stability in formulations and having a good toxicological profile.

In the field of hair dyeing, para-phenylenediamine and para-tolylenediamine are oxidation bases that are widely used. They give varied shades with oxidation couplers.

However, there is a need to discover novel oxidation bases that have a better toxicological profile than para-phenylenediamine and para-tolylenediamine, while at the same time giving the hair excellent properties in terms of color intensity, variety of shades, color uniformity, and fastness with respect to external agents.

It is already known practice to use para-phenylenediamine derivatives substituted with a pyrrolidine group as oxidation bases for dyeing keratin fibers, to replace para-phenylenediamine. For example, U.S. Pat. No. 5,851,237 describes the use of 1-(4-aminophenyl)pyrrolidine derivatives optionally substituted on the benzene nucleus. U.S. Pat. No. 5,993,491 proposes the use of N-(4-aminophenyl)-2-hydroxymethylpyrrolidine derivatives optionally substituted on the benzene nucleus and on the pyrrolidine heterocycle in position 4 with a hydroxyl radical.

Patent application JP 11-158 048 proposes compositions containing at least one compound chosen from para-phenylenediamine derivatives optionally substituted on the benzene nucleus, and one of the nitrogen atoms of which is included in a 5- to 7-membered carbon ring.

Patent application WO-02/45675 describes para-phenylenediamine compounds in which one of the amino groups forms a pyrrolidine ring substituted in the 3 position with an alkylammonium radical.

However, few, if any, of these compounds make it possible to give the hair a coloration that is equivalent in quality to that obtained with para-phenylenediamine or with para-tolylenediamine due to the lack of intensity and color uniformity.

Thus, the present inventors propose a compound and a dye composition that do not have the drawbacks of the oxidation bases of the prior art. For example, the presently claimed oxidation bases have both a good toxicological profile and desirable properties so that the dye compositions comprising them do not degrade the keratin fibers, while at the same time being capable of generating intense colorations in varied shades, which are unselective and particularly resistant.

Thus, disclosed herein is a compound of formula (I)

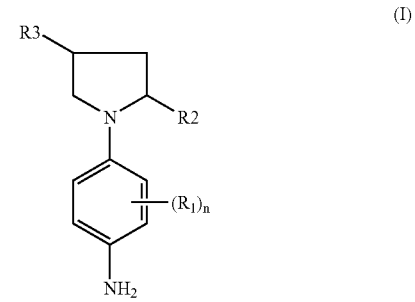

(I)

wherein:
n ranges from 0 to 4, wherein when n is greater than or equal to 2, then the radicals $R_1$ may be identical or different;
$R_1$ is chosen from halogen atoms; an onium radical Z; and $C_1$–$C_8$ aliphatic and alicyclic, saturated and unsaturated hydrocarbon-based chains, optionally comprising at least one entity chosen from oxygen, nitrogen, silicon and sulphur atoms and an $SO_2$ group, the hydrocarbon-based chains optionally being substituted with at least one radical chosen from hydroxyl, ($C_1$–$C_4$)oxyalkyl, amino, mono-($C_1$–$C_4$)aminoalkyl, and -di($C_1$–$C_4$)aminoalkyl radicals; wherein the radical $R_1$ does not comprise a peroxide bond or diazo, nitro or nitroso radicals;
$R_2$ is chosen from an onium radical Z; a carboxyl radical; a ($C_1$–$C_4$)carboxyalkyl radical; a carbamoyl radical; a ($C_1$–$C_4$)carbamoyl(alkyl) radical; ($C_1$–$C_4$)carbamoyl(dialkyl) radical; a $C_1$–$C_6$ alkyl radical; a $C_1$–$C_6$ alkyl radical optionally unsaturated, substituted with at least one radical chosen from hydroxyl, $(C_1–C_4)$alkyloxy, amino, mono-$(C_1–C_4)$alkylamino, di-$(C_1–C_4)$alkylamino, thiol, $(C_1–C_4)$alkylsulphonic and halogen radicals; a $C_1–C_6$ alkyl radical, optionally unsaturated, substituted with at least one radical chosen from carboxylic, $(C_1–C_4)$alkylcarbonyl, $(C_1–C_4)$alkyloxycarbonyl, carbamoyl, mono-$(C_1–C_4)$alkylcarbamoyl and di$(C_1–C_4)$alkylcarbamoyl radicals; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and $R_3$ is chosen from an onium radical Z; a hydrogen atom; a hydroxyl radical; a $(C_1–C_4)$alkyloxy radical; an amino radical; a mono-$(C_1–C_4)$alkylamino radical, a di$(C_1–C_4)$alkylamino radical; a thiol radical; a carboxyl radical; a $(C_1–C_4)$alkylcarboxyl radical; a carbamoyl radical; a $(C_1–C_4)$alkylcarbamoyl radical, a di$(C_1–C_4)$alkylcarbamoyl radical; a $(C_1–C_6)$alkylsulphonyl radical; a $C_1–C_6$ alkyl radical; a $C_1–C_6$ alkyl radical, optionally unsaturated, substituted with at least one radical chosen from hydroxyl, $(C_1–C_4)$alkyloxy, amino, mono-$(C_1–C_4)$alkylamino, di$(C_1–C_4)$alkylamino, thiol, $(C_1–C_4)$alkylsulphonic and halogen radicals; a $C_1–C_6$ alkyl radical, optionally unsaturated, substituted with at least one radical chosen from carboxylic, $(C_1–C_6)$alkylcarbonyl, $(C_1–C_6)$alkyloxycarbonyl, carbamoyl, mono-$(C_1–C_6)$alkylcarbamoyl, and di$(C_1–C_6)$alkylcarbamoyl radicals, and with at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms, wherein at least one of the groups $R_2$ and $R_3$ is chosen from an onium radical Z, wherein the onium radical Z is a nitrogen-based quaternary radical, Also disclosed herein is an intermediate nitro compound from the synthesis of the compounds of formula (I).

Further disclosed herein is a dye composition comprising at least one compound of formula (I) as an oxidation base.

Finally, disclosed herein is a process for dyeing keratin fibers, for example, human keratin fibers such as hair, using the disclosed composition.

The disclosed composition, for example, makes it possible to obtain a chromatic, powerful, unselective and fast coloration of keratin fibers.

In the context of the present disclosure, an aliphatic hydrocarbon-based chain may be a linear or branched chain that may comprise unsaturations of the alkene or alkyne type. An alicyclic hydrocarbon-based chain is a saturated or unsaturated, branched chain not containing an aromatic cyclic structure.

The term "onium" means a nitrogen-based quaternary radical.

When n is equal to 0, then the aromatic ring is substituted solely with the amino groups para to each other.

When n is other than 0, $R_1$ may be chosen from, for example, a chlorine atom, and from methyl, ethyl, isopropyl, vinyl, allyl, methoxymethyl, hydroxyethyl, 1-carboxymethyl, 1-aminomethyl, 2-carboxyethyl, 2-hydroxyethyl, 3-hydroxypropyl, 1,2-dihydroxyethyl, 1-hydroxy-2-amino-ethyl, 1-amino-2-hydroxyethyl, 1,2-diaminoethyl, methoxy, ethoxy, allyloxy and 2-hydroxyethyloxy radicals.

According to another embodiment, $R_1$ is chosen from $C_1–C_4$ alkyl, $C_1–C_4$ hydroxyalkyl, $C_1–C_4$ aminoalkyl, $C_1–C_4$ alkoxy and $C_1–C_4$ hydroxyalkoxy radicals. By way of example, $R_1$ may be chosen from methyl, hydroxymethyl, 2-hydroxyethyl, 1,2-dihydroxyethyl, methoxy, isopropyloxy and 2-hydroxyethoxy radicals.

The onium radical Z is, according to a further embodiment, a radical of formula (II)

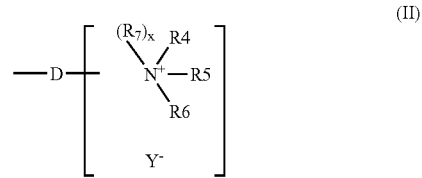

wherein:

D is a linker arm chosen from a covalent bond and linear and branched $C_1–C_{14}$ alkylene chains which are optionally interrupted with at least one hetero atom chosen from oxygen, sulphur and nitrogen, and optionally substituted with at least one radical chosen from hydroxyl, $C_1–C_6$ alkoxy and amino radicals, and which optionally bear at least one carbonyl function;

$R_4$, $R_5$ and $R_6$, taken separately, are chosen from $C_1–C_{15}$ alkyl radicals; $C_1–C_6$ monohydroxyalkyl radicals; $C_2–C_6$ polyhydroxyalkyl radicals; $(C_1–C_6)$alkoxy-$(C_1–C_6)$alkyl radicals; aryl radicals; benzyl radicals; $C_1–C_6$ amidoalkyl radicals; tri$(C_1–C_6)$alkylsilane $(C_1–C_6)$alkyl radicals; $C_1–C_6$ aminoalkyl radicals; and $C_1–C_6$ aminoalkyl radicals wherein the amine is mono- or disubstituted with a radical chosen from $C_1–C_4$ alkyl, $(C_1–C_6)$alkylcarbonyl, carbamoyl and $(C_1–C_6)$alkylsulphonyl radicals;

$R_4$, $R_5$ and $R_6$ together, in pairs, form, with the nitrogen atom to which they are attached, a saturated 4-, 5-, 6- or 7-membered carbon-based cationic ring optionally comprising at least one hetero atom such as, for example, an azetidine ring, a pyrrolidine ring, a piperidine ring, a piperazine ring or a morpholine ring, the cationic ring optionally being substituted with a halogen atom and/or with a radical chosen from a hydroxyl radical, a $C_1–C_6$ alkyl radical, a $C_1–C_6$ monohydroxyalkyl radical, a $C_2–C_6$ polyhydroxyalkyl radical, a $C_1–C_6$ alkoxy radical, a tri$(C_1–C_6)$alkylsilane$(C_1–C_6)$ alkyl radical, a carbamoyl radical, a carboxyl radical, a $(C_1–C_6)$alkylcarbonyl radical, a thio (—SH) radical, a $C_1–C_6$ thioalkyl (—R—SH) radical, a $(C_1–C_6)$alkylthio radical, an amino radical, and an amino radical mono- or disubstituted with a radical chosen from $(C_1–C_6)$ alkyl, $(C_1–C_6)$alkylcarbonyl, carbamoyl and $(C_1–C_6)$ alkylsulphonyl radicals;

$R_7$ is chosen from $C_1–C_6$ alkyl radicals; $C_1–C_6$ monohydroxyalkyl radicals; $C_2–C_6$ polyhydroxyalkyl radicals; aryl radicals; benzyl radicals; $C_1–C_6$ aminoalkyl radicals; $C_1–C_6$ aminoalkyl radicals wherein the amine is mono- or disubstituted with a radical chosen from $(C_1–C_6)$alkyl, $(C_1–C_6)$alkylcarbonyl, carbamoyl and $(C_1–C_6)$alkylsulphonyl radicals; $C_1–C_6$ carboxyalkyl radicals; $C_1–C_6$ carbamylalkyl radicals; $C_1–C_6$ trifluoroalkyl radicals; tri$(C_1–C_6)$alkylsilane$(C_1–C_6)$alkyl radicals; $C_1–C_6$ sulphonamidoalkyl radicals; $(C_1–C_6)$ alkylcarboxy($C_1$–$C_6$)alkyl radicals; ($C_1$–$C_6$)-alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N—($C_1$–$C_6$)alkylcarbamyl($C_1$–$C_6$)alkyl radicals; and N—($C_1$–$C_6$)alkylsulphonamido($C_1$–$C_6$)alkyl radicals;

x is 0 or 1, wherein:
when x=0, then the linker arm D is attached to the nitrogen atom bearing the radicals $R_4$ to $R_6$,
when x=1, then two of the radicals $R_4$ to $R_6$ form, together with the nitrogen atom to which they are attached, a 4-, 5-, 6- or 7-membered saturated ring and the linker arm D is linked to a carbon atom of the saturated ring; and $Y^-$ is a counterion.

In formula (II), when x is equal to 0, then $R_4$, $R_5$ and $R_6$, separately, are, for example, chosen from $C_1$–$C_6$ alkyl radicals, $C_1$–$C_4$ monohydroxyalkyl radicals, $C_2$–$C_4$ polyhydroxyalkyl radicals, ($C_1$–$C_6$)alkoxy($C_1$–$C_4$)alkyl radicals, $C_1$–$C_6$ carbamoylalkyl radicals, and tri($C_1$–$C_6$)alkylsilane($C_1$–$C_6$)alkyl radicals, or $R_4$ and $R_5$ together form a ring chosen from azetidine, pyrrolidine, piperidine, piperazine and morpholine rings, $R_6$ being chosen in this case from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals, aminoalkyl radicals mono- or disubstituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamylalkyl radicals; tri($C_1$–$C_6$)alkylsilane-($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamyl($C_1$–$C_6$)alkyl radicals.

When x is equal to 1, then $R_7$ is chosen from, for example, $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamyl($C_1$–$C_6$)alkyl radicals; $R_4$ and $R_5$ together form a ring chosen from azetidine, pyrrolidine, piperidine, piperazine and morpholine rings, $R_6$ being chosen in this case from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals, $C_1$–$C_6$ aminoalkyl radicals wherein the amine is mono- or disubstituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamyl($C_1$–$C_6$)alkyl radicals.

When the radical $R_2$ corresponds to formula (II), it is, for example, a trialkylammonium radical, the alkyl radicals of which may be optionally substituted.

In formula (II), D is, for example, a single bond or a $C_1$–$C_8$ alkylene chain that may be substituted.

According to yet another embodiment, the onium radical Z corresponds to formula (III)

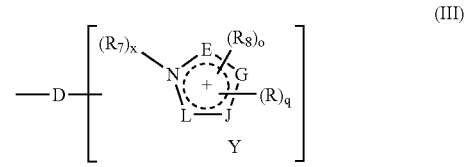

wherein:
D is a linker arm chosen from a covalent bond and linear and branched $C_1$–$C_{14}$ alkylene chains that are optionally interrupted with at least one hetero atom chosen from oxygen, sulphur and nitrogen, optionally substituted with at least one radical chosen from hydroxyl, $C_1$–$C_6$ alkoxy and amino radicals, and optionally bear at least one carbonyl function;

the ring members E, G, J and L, which may be identical or different, are chosen from carbon, oxygen, sulphur and nitrogen atoms to form a ring chosen from pyrrole, pyrazole, imidazole, triazole, oxazole, isoxazole, thiazole and isothiazole rings;

q is an integer ranging from 1 to 4;

o is an integer ranging from 1 to 3;

the sum of q+o is an integer ranging from 2 to 4;

R, which may be identical or different, is chosen from hydrogen and halogen atoms, hydroxyl radicals, $C_1$–$C_6$ alkyl radicals, $C_1$–$C_6$ monohydroxyalkyl radicals; $C_2$–$C_6$ polyhydroxyalkyl radicals; $C_1$–$C_6$ alkoxy radicals; tri($C_1$–$C_6$)alkylsilane($C_1$–$C_6$)alkyl radicals; carbamoyl radicals; carboxyl radicals; $C_1$–$C_6$ alkylcarbonyl radicals; thio radicals; $C_1$–$C_6$ thioalkyl radicals; ($C_1$–$C_6$)alkylthio radicals; amino radicals; carbamoyl radicals mono- or disubstituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ monohydroxyalkyl radicals; and $C_2$–$C_6$ polyhydroxyalkyl radicals; wherein the radicals R are borne by a carbon atom;

$R_8$, which may be identical or different, is chosen from a hydrogen atom, $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radicals, $C_1$–$C_6$ carbamylalkyl radicals, ($C_1$–$C_6$)alkylcarboxy($C_1$–$C_6$)alkyl radicals, and benzyl radicals; wherein the radicals $R_8$ are borne by a nitrogen atom, $R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is substituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)-alkylsulphinyl($C_1$–$C_6$)alkyl radicals; ($C_1$–$C_6$)alkylsulphonyl($C_1$–$C_6$)alkyl radicals; ($C_1$–$C_6$)alkylcarbonyl($C_1$–$C_6$)alkyl radicals; N—($C_1$–$C_6$)alkylcarbamyl($C_1$–$C_6$)alkyl radicals; and N—($C_1$–$C_6$)alkylsulphonamido($C_1$–$C_6$)alkyl radicals;

x is 0 or 1, wherein:
when x=0, the linker arm D is attached to the nitrogen atom, when x=1, the linker arm D is attached to one of the ring members E, G, J or L; and Y⁻ is a counterion.

By way of example, the ring members E, G, J and L may form a pyrrole, imidazole, pyrazole, oxazole, thiazole or triazole ring, and for example, an imidazole ring.

For example, the radicals $R_2$ of formula (III) may be those wherein x is equal to 0 and D is chosen from a covalent bond and a $C_1$–$C_8$ alkylene chain that may be optionally substituted.

According to another embodiment, the onium radical Z corresponds to formula (IV)

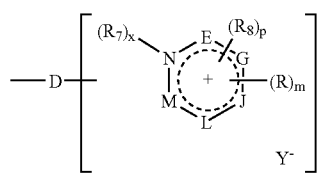

wherein:

D is a linker arm chosen from a covalent bond and linear and branched $C_1$–$C_{14}$ alkylene chains which are optionally interrupted with at least one hetero atom chosen from oxygen, sulphur and nitrogen atoms, optionally substituted with at least one radical chosen from hydroxyl, $C_1$–$C_6$ alkoxy and amino radicals, and optionally comprise at least one carbonyl function;

the ring members E, G, J, L and M, which are identical or different, are chosen from carbon, oxygen, sulphur and nitrogen atoms and form a ring chosen from pyridine, pyrimidine, pyrazine, triazine and pyridazine rings;

p is an integer ranging from 1 to 3;

m is an integer ranging from 1 to 5;

p+m is an integer ranging from 2 to 5;

R, which may be identical or different, is chosen from hydrogen and halogen atoms and from hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, carboxyl radicals, $C_1$–$C_6$ alkylcarbonyl radicals, thio radicals, $C_1$–$C_6$ thioalkyl radicals, ($C_1$–$C_6$)alkylthio radicals, amino radicals, amino radicals substituted with a radical chosen from ($C_1$–$C_6$)alkyl, ($C_1$–$C_6$)alkylcarbonyl, carbamoyl and ($C_1$–$C_6$)alkylsulphonyl radicals, $C_1$–$C_6$ monohydroxyalkyl radicals, and $C_2$–$C_6$ polyhydroxyalkyl radicals; wherein the radicals R are borne by a carbon atom, $R_8$, which may be identical or different, is chosen from a hydrogen atom, $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$)alkoxy($C_1$–$C_6$)alkyl radical, $C_1$–$C_6$ carbamylalkyl radicals, ($C_1$–$C_6$)alkylcarboxy($C_1$–$C_6$)alkyl radicals; and benzyl radicals; wherein the radicals $R_8$ are borne by a nitrogen atom;

$R_7$ is chosen from $C_1$–$C_6$ alkyl radicals, $C_1$–$C_6$ monohydroxyalkyl radicals, $C_2$–$C_6$ polyhydroxyalkyl radicals, aryl radicals, benzyl radicals, $C_1$–$C_6$ aminoalkyl radicals, $C_1$–$C_6$ aminoalkyl radicals wherein the amine is mono- or disubstituted with a radical chosen from ($C_1$–$C_6$)alkyl, ($C_1$–$C_6$)alkylcarbonyl, carbamoyl and ($C_1$–$C_6$)alkylsulphonyl radicals, $C_1$–$C_6$ carboxyalkyl radicals; $C_1$–$C_6$ carbamylalkyl radicals, $C_1$–$C_6$ trifluoroalkyl radicals, tri($C_1$–$C_6$)alkylsilane($C_1$–$C_6$)alkyl radicals, $C_1$–$C_6$ sulphonamidoalkyl radicals, ($C_1$–$C_6$)alkylcarboxy($C_1$–$C_6$)alkyl radicals, ($C_1$–$C_6$)alkylsulphinyl($C_1$–$C_6$)alkyl radicals, ($C_1$–$C_6$)alkylsulphonyl ($C_1$–$C_6$)alkyl radicals, ($C_1$–$C_6$)alkylcarbonyl($C_1$–$C_6$) alkyl radicals, N—($C_1$–$C_6$)alkylcarbamoyl($C_1$–$C_6$) alkyl radicals, and N—($C_1$–$C_6$)alkylsulphonamido ($C_1$–$C_6$)alkyl radicals;

x is 0 or 1, wherein:
when x=0, the linker arm D is attached to the nitrogen atom,
when x=1, the linker arm D is attached to one of the ring members E, G, J, L or M; and Y⁻ is a counterion.

For example, the ring members E, G, J, L and M form with the nitrogen of the ring a pyridine or pyrimidine ring.

When x is equal to 0, then R is, for example, chosen from hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, $C_1$–$C_6$alkylcarbonyl radicals, amino radicals, amino radicals mono- or disubstituted with a radical chosen from ($C_1$–$C_6$)alkyl, ($C_1$–$C_6$)alkylcarbonyl, carbamoyl and ($C_1$–$C_6$)alkylsulphonyl radicals, $C_1$–$C_6$ monohydroxyalkyl radical, and $C_2$–$C_6$ polyhydroxyalkyl radicals; and $R_8$ is chosen from $C_1$–$C_6$ alkyl radicals, $C_1$–$C_6$ monohydroxyalkyl radicals, $C_2$–$C_6$ polyhydroxyalkyl radicals, tri($C_1$–$C_6$)alkylsilane($C_1$–$C_6$)alkyl radicals, ($C_1$–$C_6$) alkoxy($C_1$–$C_6$)alkyl radicals and $C_1$–$C_6$ carbamylalkyl radicals.

When x is equal to 1, $R_7$ is, for example, chosen from $C_1$–$C_6$ alkyl radicals, $C_1$–$C_6$ monohydroxyalkyl radicals, $C_2$–$C_6$ polyhydroxyalkyl radicals, $C_1$–$C_6$ aminoalkyl radicals, $C_1$–$C_6$ aminoalkyl radicals wherein the amine is mono- or disubstituted with a radical chosen from ($C_1$–$C_6$)alkyl, ($C_1$–$C_6$)alkylcarbonyl, carbamoyl, and ($C_1$–$C_6$)alkylsulphonyl radicals, $C_1$–$C_6$ carbamylalkyl radicals, tri($C_1$–$C_6$)alkylsilane($C_1$–$C_6$)alkyl radicals, ($C_1$–$C_6$)alkylcarbonyl($C_1$–$C_6$) alkyl radicals, and N—($C_1$–$C_6$)alkylcarbamyl($C_1$–$C_6$)alkyl radicals; R is chosen from hydroxyl radicals, a $C_1$–$C_6$ alkyl radical, a $C_1$–$C_6$ monohydroxyalkyl radical, a $C_2$–$C_6$ polyhydroxyalkyl radical, $C_1$–$C_6$ alkoxy radicals, tri($C_1$–$C_6$) alkylsilane($C_1$–$C_6$)alkyl radicals, carbamoyl radicals, $C_1$–$C_6$ alkylcarbonyl radicals, and amino radicals, amino radicals mono- or disubstituted with ($C_1$–$C_6$)alkyl, ($C_1$–$C_6$)alkylcarbonyl, carbamoyl or ($C_1$–$C_6$)alkylsulphonyl radicals; and $R_8$ is chosen from $C_{1-6}$ alkyl radicals, $C_1$–$C_6$ monohydroxyalkyl radicals, $C_2$–$C_6$ polyhydroxyalkyl radicals, tri($C_1$–$C_6$) alkylsilane($C_1$–$C_6$)alkyl radicals, ($C_1$–$C_6$)alkoxy($C_1$–$C_6$) alkyl radicals and $C_1$–$C_6$ carbamylalkyl radicals.

For example, R and $R_8$ are hydrogen atoms, alkyl radicals that may be substituted, for example by at least one radical chosen from hydroxyl, amino, alkylamino, and alkoxy radicals. $R_7$ is, for example, an alkyl radical that may be substituted.

According to a further embodiment, only one of the $R_2$ or $R_3$ groups represents Z.

According to another embodiment, $R_2$ is an onium radical Z and $R_3$ is chosen from hydrogen atoms, hydroxyl radicals, amino radicals, amino radicals mono- or disubstituted with a radical chosen from ($C_1$–$C_6$)alkyl, ($C_1$–$C_6$)alkylcarbonyl, carbamoyl, and ($C_1$–$C_6$)alkylsulphonyl radicals.

According to still yet another embodiment, $R_3$ is an onium radical Z and $R_2$ is chosen from a $C_1$–$C_4$ hydroxyalkyl radical, a carbamoyl radical, a mono($C_1$–$C_4$)alkylcarbamoyl radical, a di($C_1$–$C_4$)alkylcarbamoyl radical, a carboxyl radical, a ($C_1$–$C_4$)alkyloxycarbonyl radical, a $C_1$–$C_4$ aminoalkyl radical, and a $C_1$–$C_4$ aminoalkyl radical wherein the amine is mono- or disubstituted with a $C_1$–$C_4$ alkyl radical.

According to another embodiment, $R_2$ and $R_3$ are onium radicals Z.

In the context of the disclosure, the counterion $Y^-$ may be chosen from a halogen atom, such as, bromine, chlorine, fluorine or iodine, a hydroxide, a citrate, a succinate, a tartrate, a lactate, a tosylate, a mesylate, a benzenesulphonate, an acetate, and a hydrogen sulphate or a $C_1$–$C_6$ alkyl sulphate such as, for example, methyl sulphate or ethyl sulphate.

Examples of derivatives of formula (I) that may be mentioned include:

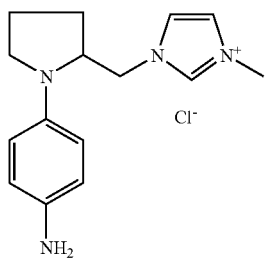

1-{[1-(4-aminophenyl)pyrrolidin-2-yl]methyl}-3-methyl-1H-imidazol-3-ium chloride

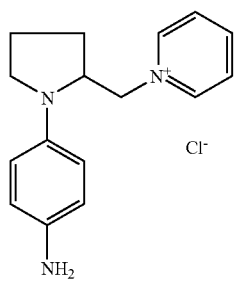

1-{[1-(4-aminophenyl)pyrrolidin-2-yl]methyl}pyridinium chloride

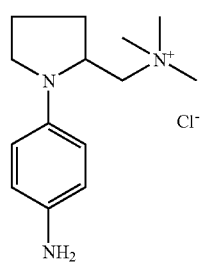

[1-(4-aminophenyl)pyrrolidin-2-yl]-N,N,N-trimethylmethanaminium chloride

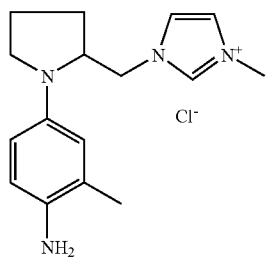

1-{[1-(4-amino-3-methylphenyl)pyrrolidin-2-yl]methyl}-3-methyl-1H-imidazol-3-ium chloride

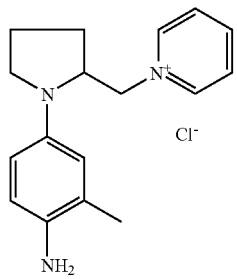

1-{[1-(4-amino-3-methylphenyl)pyrrolidin-2-yl]methyl}pyridinium chloride

-continued

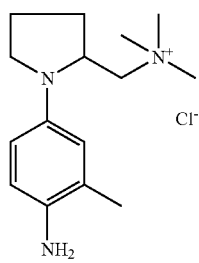
[1-(4-amino-3-methylphenyl)pyrrolidin-2-yl]-N,N,N-trimethylmethanaminium chloride

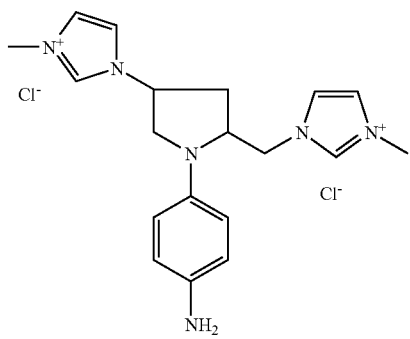
1-[1-(4-aminophenyl)-5-(3-methyl-1H-imidazol-3-ium-1-ylmethyl)pyrrolidin-3-yl] 3-methyl-1H-imidazol-3-ium dichloride

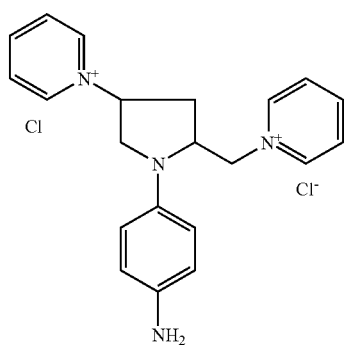
1-[1-(4-aminophenyl)-5-(pyridinium-1-ylmethyl)pyrrolidin-3-yl]pyridinium dichloride

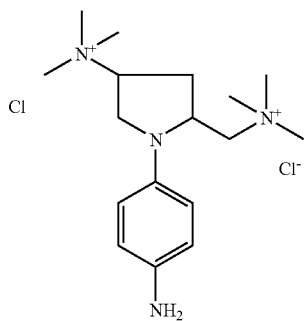
1-(4-aminophenyl)-N,N,N-trimethyl-5-[(trimethylammonio)methyl]pyrrolidin-3-aminium chloride

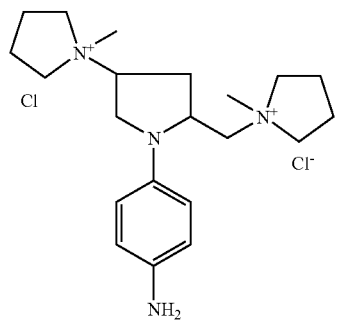
1-[1-(4-aminophenyl)-5-(N-methylpyrrilidinium-1-ylmethyl)pyrrolidin-3-yl] N-methylpyrrilidinium dichloride -continued

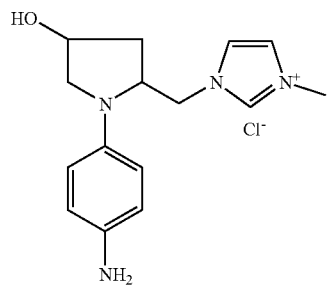

1-{[1-(4-aminophenyl)-4-hydroxypyrrolidin-2-yl]methyl}-3-methyl-1H-imidazol-3-ium chloride

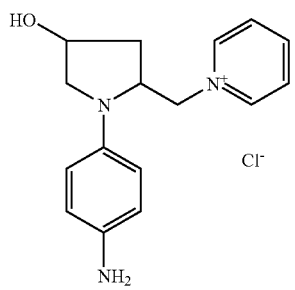

1-{[1-(4-aminophenyl)-4-hydroxypyrrolidin-2-yl]methyl}pyridinium chloride

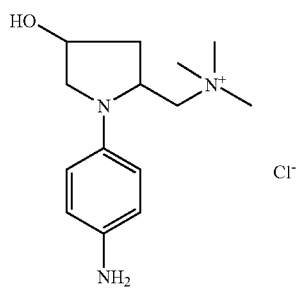

[1-(4-aminophenyl)-4-hydroxypyrrolidin-2-yl]-N,N,N-trimethylmethanaminium chloride

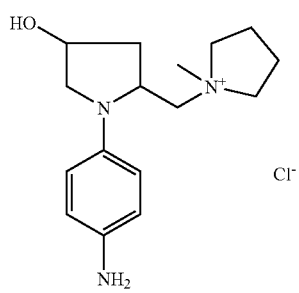

1-[1-(4-Amino-phenyl)-4-hydroxy-pyrrolidin-2-ylmethyl]-1methyl-pyrrolidinium chloride

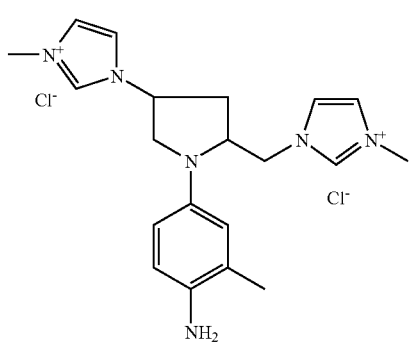

1-[1-(4-amino-3-methylphenyl)-5-(3-methyl-1H-imidazol-3-ium-1-ylmethyl)pyrrolidin-3-yl]-3-methyl-1H-imidazol-3-ium dichloride -continued

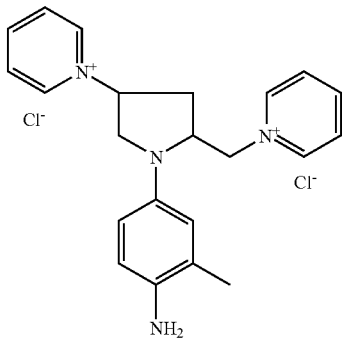

1-[1-(4-amino-3-methylphenyl)-5-(pyridinium-1-ylmethyl)pyrrolidin-3-yl]pyridinium dichloride

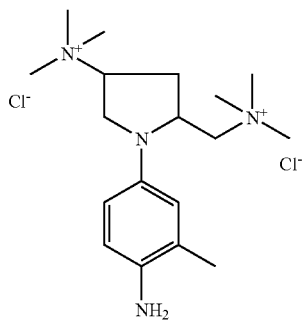

1-(4-amino-3-methylphenyl)-N,N,N-trimethyl-5-[(trimethylammonio)methyl]pyrrolidin-3-aminium dichloride

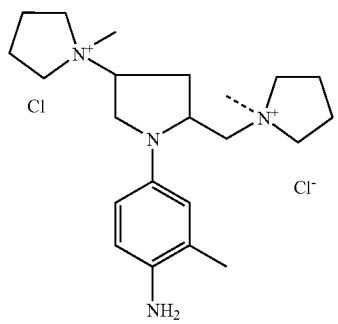

1-[1-(4-amino-3-methylphenylphenyl)-5-(Nmethylpyrrilidinium-1-ylmethyl)pyrrolidin-3-yl] Nmethylpyrrilidinium dichloride

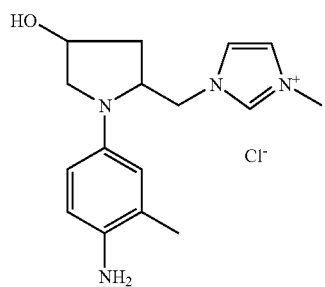

1-{[1-(4-amino-3-methylphenyl)-4-hydroxypyrrolidin-2-yl]methyl}-3-methyl-1H-imidazol-3-ium chloride

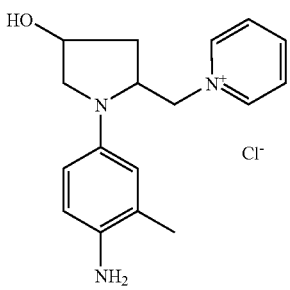

1-{[1-(4-amino-3-methylphenyl)-4-hydroxypyrrolidin-2-yl]methyl}pyridinium chloride -continued
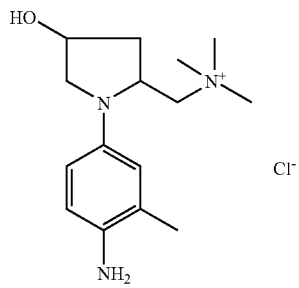
[1-(4-amino-3-methylphenyl)-4-hydroxypyrrolidin-2-yl]-N,N,N-trimethylmethanaminium chloride
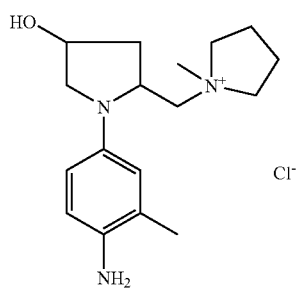
1-[1-(4-Amino-3-methylphenyl)-4-hydroxy-pyrrolidin-2ylmethyl]-1-methylpyrrolidinium chloride
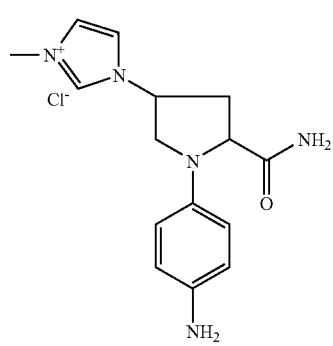
1-(4-aminophenyl)-4-(3-methyl-1H-imidazol-3-ium-1-yl)prolinamide chloride
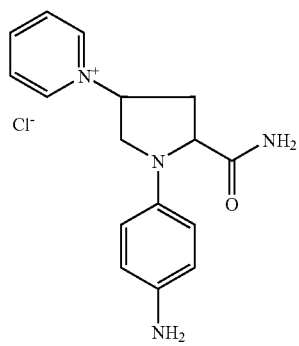
1-(4-aminophenyl)-4-pyridinium-1-ylprolinamide chloride
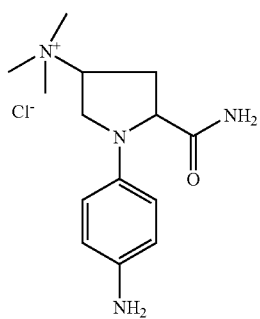
[1-(4-Amino-phenyl)-5-carbamoylpyrrolidin-3-yl]-trimethylammonium chloride -continued
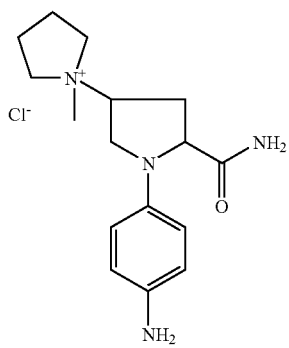
1'-(4-Aminophenyl)-5'-carbamoyl-1-methyl-[1,3']bipyrrolidinyl-1-ium chloride
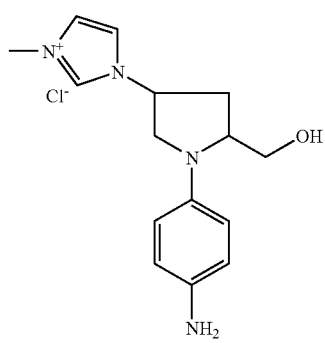
1-[1-(4-aminophenyl)-5-(hydroxymethyl)pyrrolidin-3-yl]-3-methyl-1H-imidazol-3-ium chloride
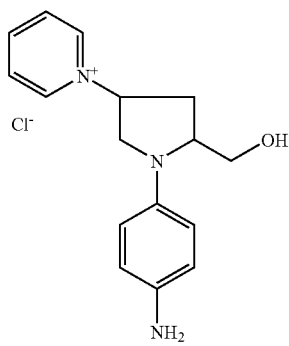
1-[1-(4-aminophenyl)-5-(hydroxymethyl)pyrrolidin-3-yl]pyridinium chloride
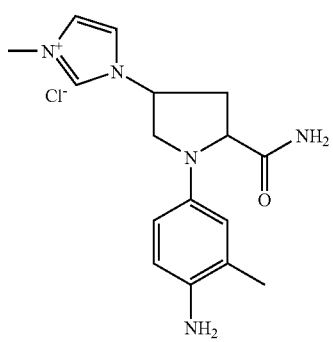
1'-(4-amino-3-methylphenyl)-4-(3-methyl-1H-imidazol-3-ium-1-yl)prolinamide chloride -continued
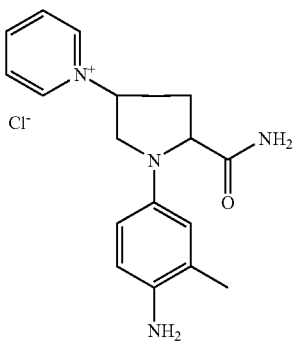
1-(4-amino-3-methylphenyl)-4-pyridinium-1-ylprolinamide chloride
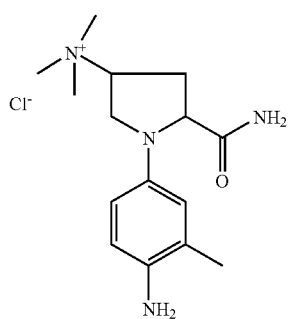
[1-(4-Amino-3-methylphenyl)-5-carbamoyl-pyrrolidin-3-yl]trimethylammonium chloride
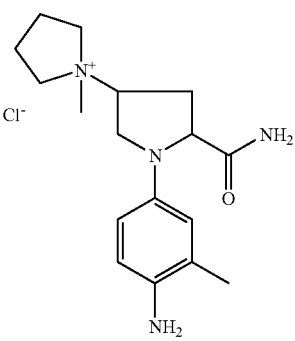
1'-(4-Amino-3-methylphenyl)-5'-carbamoyl-1-methyl-[1,3']bipyrrolidinyl-1-ium chloride
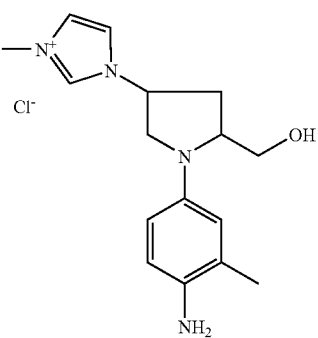
1-[1-(4-amino-3-methylphenyl)-5-(hydroxymethyl)pyrrolidin-3-yl]-3-methyl-1H-imidazol-3-ium chloride -continued
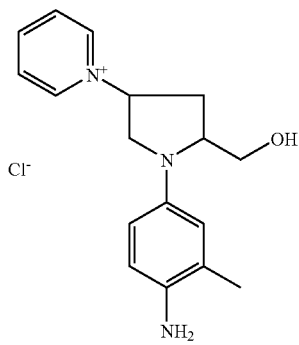
1-[1-(4-amino-3-methylphenyl)-5-(hydroxymethyl)pyrrolidin-3-yl]pyridinium chloride
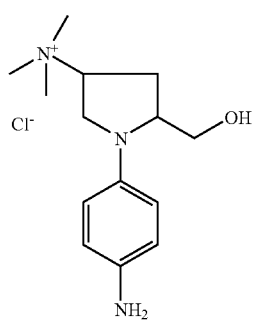
1-(4-aminophenyl)-5-(hydroxymethyl)-N,N,N-trimethylpyrrolidin-3-aminium chloride
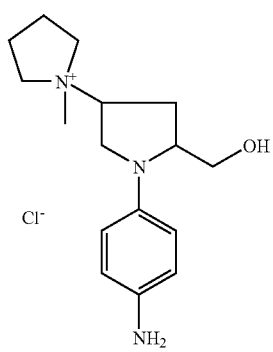
1'-(4-Amino-phenyl)-5'-hydroxymethyl-1-methyl-[1,3']bipyrrolidinyl-1-ium chloride
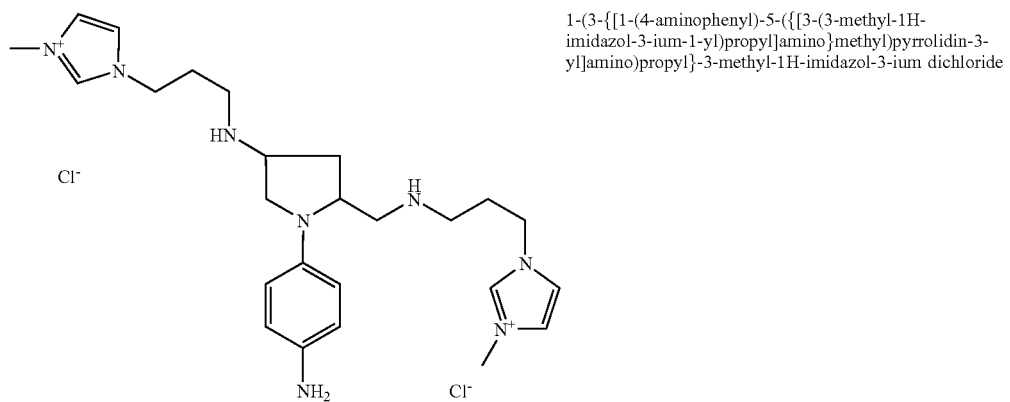
1-(3-{[1-(4-aminophenyl)-5-({[3-(3-methyl-1H-imidazol-3-ium-1-yl)propyl]amino}methyl)pyrrolidin-3-yl]amino)propyl}-3-methyl-1H-imidazol-3-ium dichloride -continued

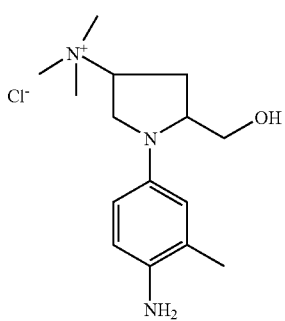

1-(4-amino-3-methylphenyl)-5-(hydroxymethyl)-N,N,N-trimethylpyrrolidin-3-aminium chloride

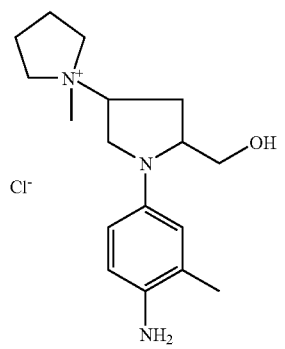

1'-(4-Amino-3-methyl-phenyl)-5'-hydroxymethyl-1-methyl-[1,3']bipyrrolidinyl-1-ium chloride

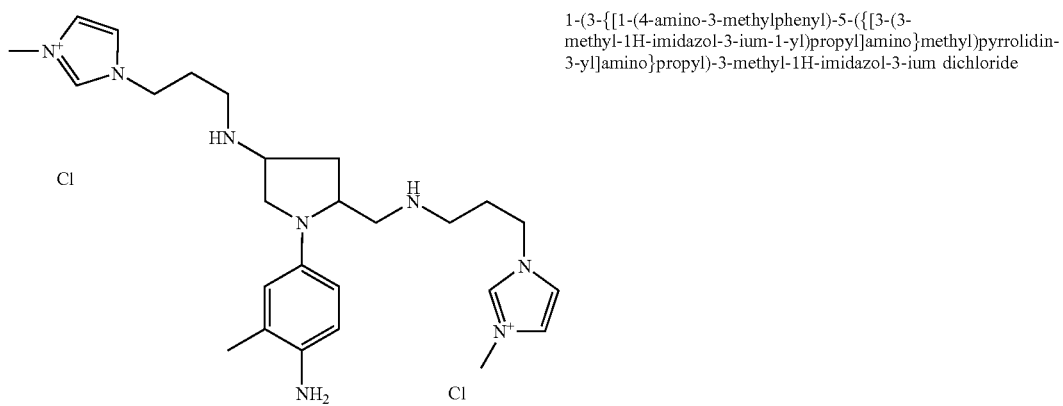

1-(3-{[1-(4-amino-3-methylphenyl)-5-({[3-(3-methyl-1H-imidazol-3-ium-1-yl)propyl]amino}methyl)pyrrolidin-3-yl]amino}propyl)-3-methyl-1H-imidazol-3-ium dichloride

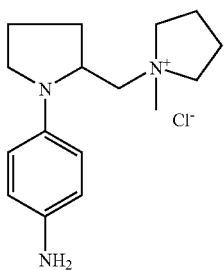

1-[1-(4-Aminophenyl)pyrrolidin-2-ylmethyl]-1-methylpyrrolidinium chloride

| | |
|---|---|
| 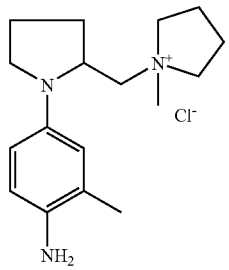 | 1-[1-(4-Amino-3-methylphenyl)pyrrolidin-2-ylmethyl]-1-methylpyrrolidinium chloride |

For example, the derivatives of formula (I) are chosen from the following compounds:

1-{[1-(4-aminophenyl)pyrrolidin-2-yl]methyl}-3-methyl-1H-imidazol-3-ium chloride,
1-{[1-(4-aminophenyl)pyrrolidin-2-yl]methyl}pyridinium chloride,
[1-(4-aminophenyl)pyrrolidin-2-yl]-N,N,N-trimethylmethanaminium chloride,
1-[1-(4-aminophenyl)-5-(3-methyl-1H-imidazol-3-ium-1-ylmethyl)pyrrolidin-3-yl]3-methyl-1H-imidazol-3-ium dichloride,
1-(4-aminophenyl)-N,N,N-trimethyl-5-[(trimethylammonio)methyl]pyrrolidin-3-amminium chloride,
1-[1-(4-aminophenyl)-5-(pyridinium-1-ylmethyl)pyrrolidin-3-yl]pyridinium dichloride,
1-{[1-(4-aminophenyl)-4-hydroxypyrrolidin-2-yl]methyl}-3-methyl-1H-imidazol-3-ium chloride,
1-{[1-(4-aminophenyl)-4-hydroxypyrrolidin-2-yl]methyl}pyridinium chloride,
[1-(4-aminophenyl)-4-hydroxypyrrolidin-2-yl]-N,N,N-trimethylmethanaminium chloride,
1-[1-(4-aminophenyl)-4-hydroxypyrrolidin-2-ylmethyl]-1-methyl-pyrrolidinium chloride,
1-(4-aminophenyl)-4-(3-methyl-1H-imidazol-3-ium-1-yl) prolinamide chloride,
1-(4-aminophenyl)-4-pyridinium-1-ylprolinamide chloride,
[1-(4-aminophenyl)-5-carbamoylpyrrolidin-3-yl]-trimethylammonium chloride,
1'-(4-aminophenyl)-5'-carbamoyl-1-methyl-[1,3']bipyrrolidinyl-1-ium chloride,
1-[1-(4-aminophenyl)-5-(hydroxymethyl)pyrrolidin-3-yl]-3-methyl-1H-imidazol-3-ium chloride,
1'-(4-aminophenyl)-5'-hydroxymethyl-1-methyl-[1,3']bipyrrolidinyl-1-ium chloride,
1-(3-{[1-(4-aminophenyl)-5-({[3-(3-methyl-1H-imidazol-3-ium-1-yl)propyl]amino}methyl)pyrrolidin-3-yl]amino}propyl)-3-methyl-1H-imidazol-3-ium dichloride,
1-[1-(4-amino-phenyl)pyrrolidin-2-ylmethyl]-1-methylpyrrolidinium chloride, and
1-[1-(4-aminophenyl)-5-(N-methylpyrrilidinium-1-ylmethyl)pyrrolidin-3-yl]-N-methylpyrrilidinium dichloride.

The derivatives of formula (I) may be obtained, for example, via the synthetic process below, the derivative (1) being derived from a procedure described in patent FR 2 817 478:

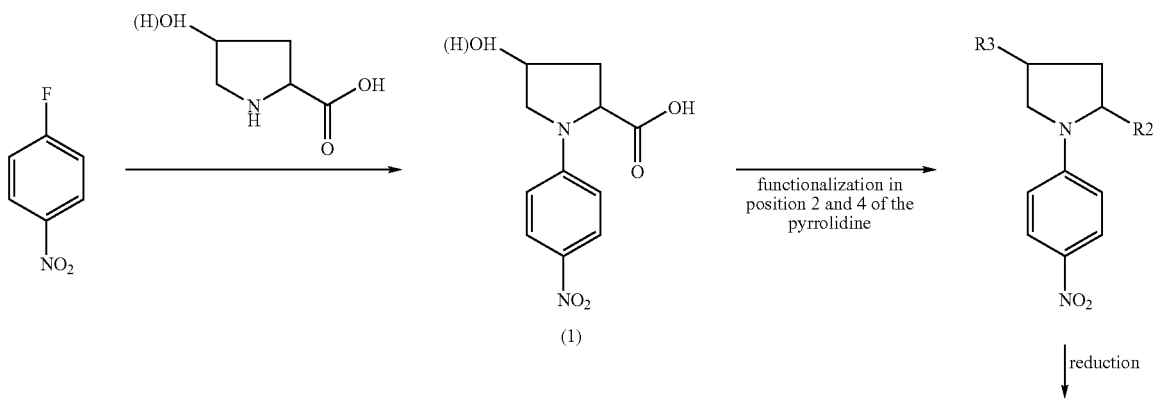

A further embodiment of the disclosure is also the nitro derivatives of formula (I') below:

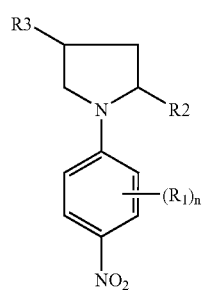

wherein $R_1$, $R_2$, $R_3$ and n are as defined above.

Another embodiment is also a composition for dyeing keratin fibers. The dye composition of the present disclosure comprises, in a medium that is suitable for dyeing keratin fibers, for example, human hair at least one oxidation base, wherein the at least one oxidation base is a compound of formula (I) as defined above.

The at least one oxidation base of the present disclosure may be present in the composition in an amount, for each oxidation base, if there are more than one, ranging from about 0.001% to about 10% by weight relative to the total weight of the dye composition, and for example, ranging from about 0.005% to about 6%.

The disclosed dye composition may further comprise at least one coupler conventionally used for dyeing keratin fibers. Among these couplers that may, for example, be mentioned are meta-phenylenediamines, meta-aminophenols, meta-diphenols, naphthalenic couplers and heterocyclic couplers, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2, 4-diaminophenoxy)propane, 3-ureido-aniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene and 2,6-bis(β-hydroxyethylamino)toluene and the acid addition salts thereof.

In the disclosed composition, the coupler(s) is (are) present in an amount ranging from about 0.001% to about 10% by weight relative to the total weight of the dye composition, and for example, ranging from about 0.005% to about 6%.

The disclosed composition may also comprise at least one additional oxidation base conventionally used in oxidation dyeing, other than those described above. By way of example, these additional oxidation bases are chosen from para-phenylenediamines other than those described above, bis(phenyl)alkylenediamines, para-aminophenols, bis-para-aminophenols, ortho-aminophenols and heterocyclic bases, and the addition salts thereof.

Among the para-phenylenediamines which can be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-α-hydroxyethylamino-5-aminotoluene and 3-hydroxy-1-(4'-aminophenyl)pyrrolidine, and the acid addition salts thereof.

Among the para-phenylenediamines mentioned above para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof may be used.

Among the bis(phenyl)alkylenediamines which can be mentioned, for example, are N,N-bis(β-hydroxyethyl)-N,N'-bis(4-aminophenyl)-1,3-diaminopropanol, N,N-bis(β-hydroxyethyl)-N,N-bis(4-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4-amino-3-methylphenyl) ethylenediamine and 1,8-bis(2,5-diaminophenoxy)-3,6-dioxaoctane, and the acid addition salts thereof.

Among the para-aminophenols which can be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols which can be mentioned, for example, are 2-aminophenol, 2-amino-5-methylphenol, 2-amino-6-methylphenol and 5-acetamido-2-aminophenol, and the acid addition salts thereof.

Among the heterocyclic bases, mention may be made, for example, of pyridine derivatives, pyrimidine derivatives and pyrazole derivatives.

Among the pyridine derivatives which may be mentioned are the compounds described, for example, in patents GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Other pyridine oxidation bases that are useful in the disclosed composition are the 3-aminopyrazolo[1,5-a]pyridine oxidation bases or the addition salts thereof described, for example, in patent application FR 2 801 308. By way of example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo-[1,5-a]pyrid-7-ol and also the addition salts thereof with an acid or with a base.

Among the pyrimidine derivatives which may be mentioned are the compounds described, for example, in German patent DE 2 359 399 or Japanese patents JP 88-169 571; JP 05 63 124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Among the pyrazole derivatives which may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenyl pyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

As defined above, the optional at least one additional oxidation base, when present, is present in an amount, for each additional oxidation base, ranging from about 0.001% to about 10% by weight relative to the total weight of the dye composition, and for example, ranging from about 0.005% to about 6%.

In general, the addition salts of the oxidation bases and of the couplers that may be used in the context of the disclosure are chosen, for example, from the acid addition salts, such as the hydrochlorides, hydrobromides, sulphates, citrates, succinates, tartrates, lactates, tosylates, benzenesulphonates, phosphates and acetates, and the base addition salts, such as sodium hydroxide, potassium hydroxide, ammonia, amines or alkanolamines.

The disclosed dye composition may also comprise at least one direct dye that may be chosen, for example, from nitrobenzene dyes, azo direct dyes and nonionic direct dyes. The direct dyes may be of nonionic, anionic or cationic nature.

The medium that is suitable for dyeing, also known as the dye support, comprises water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The solvent(s) are present in an amount, for example, ranging from about 1% to about 40% by weight relative to the total weight of the dye composition, and for example, ranging from about 5% to about 30% by weight.

The dye composition in accordance with the disclosure can also comprise various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and for example, anionic, cationic, nonionic or amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are present in an amount for each ranging from about 0.01% to about 20% by weight relative to the weight of the composition.

Needless to say, a person skilled in the art will take care to select this or these optional additional compounds such that the advantageous properties intrinsically associated with the oxidation dye composition in accordance with the disclosure are not, or are not substantially, adversely affected by the addition(s) envisaged.

The pH of the disclosed dye composition ranges from about 3 to about 12 and for example, ranging from about 5 to about 11. It may be adjusted to the desired value using acidifying or basifying agents usually used in the dyeing of keratin fibers, or optionally using standard buffer systems.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (II) below:

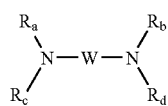

(II)

wherein W is a propylene residue which is unsubstituted or substituted with a hydroxyl group or a $C_1$–$C_4$ alkyl radical; $R_a$, $R_b$, $R_c$ and $R_d$, which may be identical or different, are chosen from a hydrogen atom, a $C_1$–$C_4$ alkyl radical or a $C_1$–$C_4$ hydroxyalkyl radical.

The disclosed dye composition may be in various forms, such as in the form of liquids, creams or gels, or in any other form that is suitable for dyeing keratin fibers, and for example, human hair.

The presently disclosed process for dyeing keratin fibers comprises applying to the fibers the disclosed composition, and developing color using an oxidizing agent. The color may be developed at acidic, neutral or alkaline pH and the oxidizing agent may be added to the disclosed composition just at the time of use, or it may be used in the form of an oxidizing composition comprising it, which is applied simultaneously or sequentially with the disclosed dye composition.

According to further embodiments, the disclosed composition is mixed, for example, at the time of use, with a composition comprising, in a medium that is suitable for dyeing, at least one oxidizing agent, this oxidizing agent being present in an amount that is sufficient to develop a coloration. The mixture obtained is then applied to the keratin fibers. After an action time ranging from about 3 to about 50 minutes, for example, ranging from about 5 to about 30 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts such as perborates and persulphates, peracids and oxidase enzymes, among which mention may be made of peroxidases, 2-electron oxidoreductases such as uricases, and 4-electron oxygenases, for instance laccases. In one embodiment, the oxidizing agent used herein is hydrogen peroxide.

The oxidizing composition may also comprise various adjuvants conventionally used in compositions for dyeing the hair and as defined above.

The pH of the oxidizing composition comprising at least the oxidizing agent is such that, after mixing with the dye composition, the pH of the resulting composition applied to the keratin fibers ranges from, for example, about 3 to about 12 approximately and, for example, ranges from about 5 to about 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels or any other form that is suitable for dyeing keratin fibers, and, for example, human hair.

Another embodiment of the disclosure is a multi-compartment kit, comprising a first compartment comprising at least the disclosed dye composition defined above and a second compartment comprising at least an oxidizing composition. This kit may be equipped with a means for applying the desired mixture to the hair, such as the devices described in patent FR-2 586 913 in the name of the Applicant.

Using this device, it is possible to dye keratin fibers using a process that includes mixing a dye composition comprising at least one oxidation base of formula (I) with an oxidizing agent, and applying the mixture obtained to the keratin fibers for a time that is sufficient to develop the desired coloration.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES

Example 1

Synthesis of 3-[1-(4-aminophenyl)pyrrolidin-2-yl]-1-methyl-3H-imidazol-1-ium chloride Synthesis of 1-methyl-3-[1-(4-nitrophenyl)pyrrolidin-2-ylmethyl]-3H-imidazol-1-ium chloride (2)

16.8 g (0.07 mol) of 2-chloromethyl-1-(4-nitrophenyl)pyrrolidine (1), 17.2 g (0.21 mol) of methylimidazole and 70 ml of toluene were refluxed for 9 hours. The solvent was

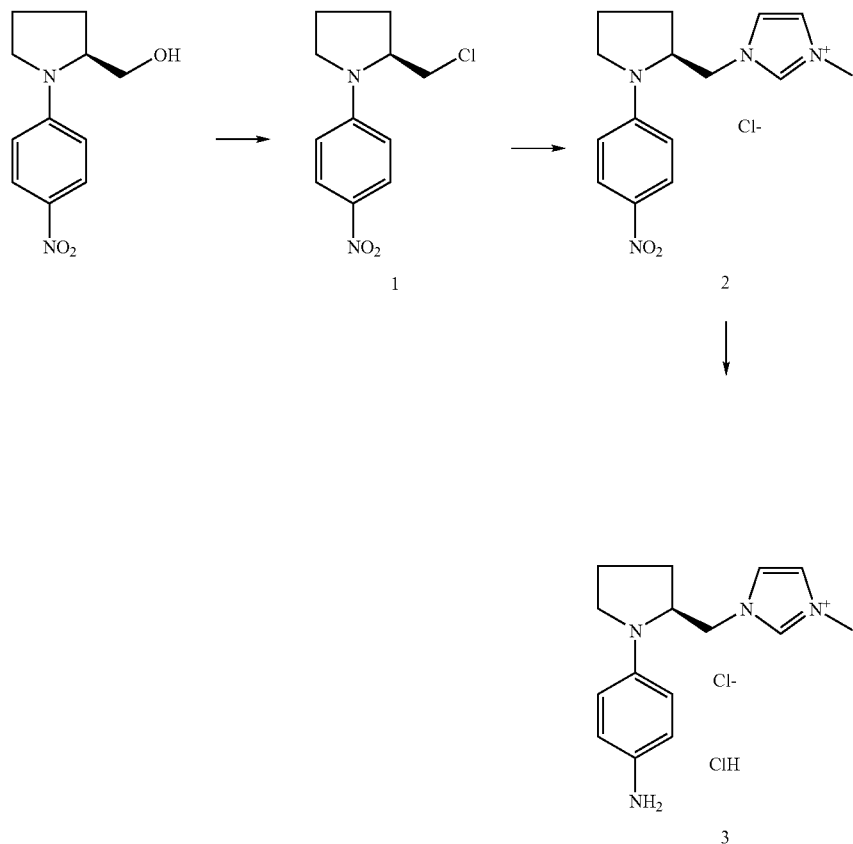

Synthesis of 2-chloromethyl-1-(4-nitrophenyl)pyrrolidine (1)

27.9 ml (0.36 mol) of mesyl chloride were added dropwise to a solution of [1-(4-nitrophenyl)pyrrolidin-2-yl]methanol (66.7 g, 0.03 mol), 300 ml of anhydrous DMF and 58.5 ml (0.42 mol) of anhydrous triethylamine, cooled in an ice bath. The temperature was allowed to rise to 20° C. over one hour with stirring. 35.2 g (0.6 mol) of sodium chloride were added and the mixture was heated at 100° C. for one hour. The reaction medium was poured into 1.4 l of ice-water. The precipitate was filtered off, washed with water, dried and recrystallized from isopropanol. 63.7 g of a yellow powder (1) were thus obtained.

$^1$H NMR (400 MHz-$D_2O$) ppm, 2.07 (m, 4H); 3.3 (m, 1H) 3.53 (m, 1H) 3.63 (m, 2H) 4.21 (m, 1H) 6.72 (m, 2H) 8.07 (m, 2H).

evaporated off and the product was recrystallized from isopropanol and then dried under vacuum. 3 g of yellow crystals (2) were obtained.

$^1$H NMR (400 MHz-$D_2O$) ppm 1.93 (m, 4H); 3.30 (m, 1H); 3.60 (m, 1H); 3.82 (s, 3H); 4.30 (m, 2H); 4.45 (m, 1H); 6.75 (d, 2H); 7.71 (s, 1H); 7.83 (d, 1H); 8.05 (d, 2H); 9.25 (s, 1H)

Synthesis of 3-[1-(4-aminophenyl)pyrrolidin-2-ylmethyl]-1-methyl-3H-imidazol-1-ium chloride hydrochloride (3)

3 g (0.093 mol) of 1-methyl-3-[1-(4-nitrophenyl)pyrrolidin-2-ylmethyl]-3H-imidazol-1-ium (2) dissolved in 350 ml of ethanol were hydrogenated in the presence of palladium-on-charcoal under a hydrogen pressure of 10 bar at a temperature of 30° C.; after filtering off the catalyst, the expected derivative (3) was isolated in the form of the hydrochloride. 2.6 g of a white powder were obtained.

¹H NMR (400 MHz-D₂O) ppm 1.66 (m, 1H); 1.89 (m, 1H); 2.01 (m, 1H); 2.13 (m, 1H); 3.17 (m, 1H); 3.54 (m, 1H); 3.73 (s, 3H); 4.23 (dd, 1H); 4.33 (m, 1H); 4.43 (dd, 1H); 6.67 (d, 2H); 7.21 (d, 2H); 7.35 (s, 1H); 7.43 (s, 1H); 8.59 (s, 1H).

Example 2

Synthesis of 1-[1-(4-aminophenyl)-5-(3-methyl-1H-imidazol-3-ium-1-ylmethyl)pyrrolidin-3-yl]-3-methyl-1H-imidazol-3-ium dimesylate (6)

dropwise. The mixture was stirred at room temperature for 5 hours. Methanol was added slowly. The reaction mixture was evaporated to dryness. The product was precipitated from saturated sodium chloride solution, filtered off and dried under vacuum. 5.33 g of a yellow powder were obtained.

¹H NMR (400 MHz-DMSO) ppm 1.95 (m, 1H); 2.20 (m, 1H); 3.14 (dd, 1H); 3.44 (m, 2H); 3.63 (m, 1H); 4.06 (m, 1H); 4.51 (m, 1H); 4.87 (m, 1H); 5.12 (m, 1H); 6.69 (d, 2H); 8.04 (d, 2H).

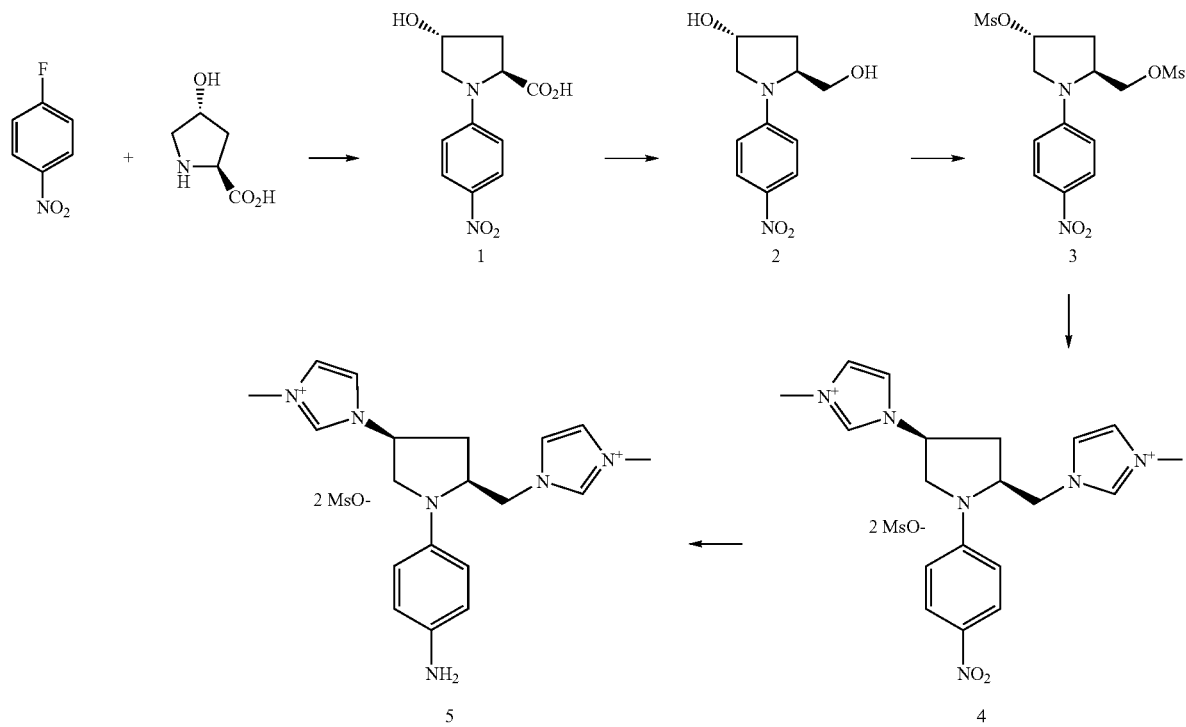

Synthesis of 4-hydroxy-1-(4-nitrophenyl)pyrrolidine-2-carboxylic acid (1)

10 g (70.9 mmol) of 4-fluoronitrobenzene, 11.75 g (85 mmol) of potassium carbonate and 9.3 g (70.8 mmol) of trans-4-hydroxyproline were stirred in 100 ml of distilled water. The mixture was refluxed for 16 hours and was then cooled to room temperature. The product was extracted with ethyl acetate. The organic phases were washed with a saturated solution, dried over sodium sulphate and concentrated under reduced pressure. The oil obtained was crystallized from an ethyl acetate/heptane mixture. A yellow powder was obtained.

¹H NMR (400 MHz-DMSO) ppm 1.99–2.30 (m, 2H); 3.68 (m, 1H); 4.46 (m, 2H); 5.27 (m, 1H); 6.58 (d, 2H); 8.07 (d, 2H)

Synthesis of 5-hydroxymethyl-1-(4-nitrophenyl)pyrrolidin-3-ol (2)

5 g (19.8 mmol) of 4-hydroxy-1-(4-nitrophenyl)pyrrolidine-2-carboxylic acid were stirred in 50 ml of THF at 3° C. 60 ml (59 mmol) of borane-THF complex were added

Synthesis of the 4-methanesulphonyloxy-1-(4-nitrophenyl)pyrrolidin-2-ylmethylmethanesulphonic ester (3)

3 g (12.6 mmol) of 5-hydroxymethyl-1-(4-nitrophenyl) pyrrolidin-3-ol and 4.6 ml (37.8 mmol) of triethylamine were stirred in 20 ml of THF at 5° C. 2.54 ml (32.8 mmol) of mesyl chloride were added slowly. The reaction mixture was stirred at room temperature for 6 hours. The product was precipitated from ice-water and recrystallized from methanol. 1.7 g of a yellow powder were obtained.

¹H NMR (400 MHz-DMSO) ppm 3.15 (s, 3H); 3.28 (s, 3H); 3.14 (dd, 1H); 3.70 (m, 1H); 4.90 (m, 1H); 4.28–4.40 (m, 2H); 4.59 (m, 1H); 5.49 (m, 1H); 6.87 (d, 2H); 8.10 (d, 2H).

Synthesis of 1-[1-(4-nitrophenyl)-5-(3-methyl-1H-imidazol-3-ium-1-ylmethyl)pyrrolidin-3-yl]-3-methyl-1H-imidazol-3-ium dimesylate (4)

1.7 g (4.3 mmol) of the 4-methanesulphonyloxy-1-(4-nitrophenyl)pyrrolidin-2-ylmethylmethanesulphonic ester (3) were heated in 15 ml of N-methylimidazole at 90° C. for 25 hours. The reaction mixture was cooled. The oil obtained was taken up in ethyl acetate and purified by preparative HPLC.

Synthesis of 1-[1-(4-aminophenyl)-5-(3-methyl-1H-imidazol-3-ium-1-ylmethyl)pyrrolidin-3-yl]-3-methyl-1H-imidazol-3-ium dimesylate (5)

After reduction with zinc/acetic acid, 1-[1-(4-aminophenyl)-5-(3-methyl-1H-imidazol-3-ium-1-ylmethyl)pyrrolidin-3-yl]-3-methyl-1H-imidazol-3-ium was obtained.
Mass ESI+: m/2z=169[M]

Examples of Dyeing

Examples 1 to 5 of Dyeing in Alkaline Medium

Each mixture obtained was applied to locks of grey hair containing 90% white hairs. After a leave-in time of 30 minutes, the locks were rinsed, washed with a standard shampoo, rinsed again and then dried.

The following dyeing results were obtained.

| Examples | 1 | 2 | 3 | 4 | 5 |
|---|---|---|---|---|---|
| Shade observed | Violet-blue | Blue-violet | Chromatic violet-red | Violet | Grey |

| Examples | 1 | 2 | 3 | 4 | 5 |
|---|---|---|---|---|---|
| 3-[1-(4-Aminophenyl)pyrrolidin-2-ylmethyl]-1-methyl-3H-imidazol-1-ium chloride hydrochloride (base) | $10^{-3}$ mol | $10^{-3}$ mol | $10^{-3}$ mol | $10^{-3}$ mol | — |
| 1-[1-(4-Aminophenyl)-5-(3-methyl-1H-imidazol-3-ium-1-ylmethyl)pyrrolidin-3-yl]-3-methyl-1H-imidazol-3-ium dimesylate (base) | — | — | — | — | $10^{-3}$ mol |
| 2-(2,4-Diaminophenoxy)ethanol dihydrochloride (coupler) | $10^{-3}$ mol | — | — | — | $10^{-3}$ mol |
| 3-Amino-2-chloro-6-methylphenol hydrochloride (coupler) | — | $10^{-3}$ mol | — | — | — |
| 3,6-Dimethyl-1H-pyrazolo[5,1-c][1,2,4]triazole (coupler) | — | — | $10^{-3}$ mol | — | — |
| 2-Methyl-5-aminophenol (coupler) | — | — | — | $10^{-3}$ mol | — |
| Dye support (1) | (*) | (*) | (*) | (*) | (*) |
| Demineralized water qs | 100 g | 100 g | 100 g | 100 g | 100 g |

| | | |
|---|---|---|
| 96° ethyl alcohol | 20.8 | g |
| Sodium metabisulphite as an aqueous 35% solution | 0.23 | g AM |
| Pentasodium salt of diethylenetriaminepentaacetic acid as an aqueous 40% solution | 0.48 | g AM |
| $C_8$–$C_{10}$ alkyl polyglucoside as an aqueous 60% solution | 3.6 | g AM |
| Benzyl alcohol | 2.0 | g |
| Polyethylene glycol containing 8 units of ethylene oxide | 3.0 | g |
| $NH_4Cl$ | 4.32 | g |
| Aqueous ammonia containing 20% $NH_3$ | 2.94 | g |

(*)Dye support (1) pH 9.5

At the time of use, each composition was mixed with an equal weight of 20-volumes aqueous hydrogen peroxide solution (6% by weight). A final pH of 9.5 was obtained.

Examples 6 to 10 of Dyeing in Acidic Medium

The following dye compositions were prepared:

| Examples | 6 | 7 | 8 | 9 | 10 |
|---|---|---|---|---|---|
| 3-[1-(4-Aminophenyl)pyrrolidin-2-ylmethyl]-1-methyl-3H-imidazol-1-ium chloride; hydrochloride (base) | $10^{-3}$ mol | $10^{-3}$ mol | $10^{-3}$ mol | $10^{-3}$ mol | — |
| 1-[1-(4-Aminophenyl)-5-(3-methyl-1H-imidazol-3-ium-1-ylmethyl)pyrrolidin-3-yl]-3-methyl-1H-imidazol-3-ium dimesylate (base) | — | — | — | — | $10^{-3}$ mol |
| 2-(2,4-Diaminophenoxy)ethanol dihydrochloride (coupler) | $10^{-3}$ mol | — | — | — | $10^{-3}$ mol |
| 3-Amino-2-chloro-6-methylphenol hydrochloride (coupler) | — | $10^{-3}$ mol | — | — | — |

| -continued | | | | | |
|---|---|---|---|---|---|
| 2-Methyl-5-aminophenol (coupler) | — | — | — | $10^{-3}$ mol | |
| 3,6-Dimethyl-1 H-pyrazolo[5,1-c][1,2,4]triazole (coupler) | — | — | $10^{-3}$ mol | — | — |
| Dye support (2) | (*) | (*) | (*) | (*) | (*) |
| Demineralized water qs | 100 g | 100 g | 100 g | 100 g | 100 g |

| | |
|---|---|
| 96° ethyl alcohol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 units of ethylene oxide | 3.0 g |
| $Na_2HPO_4$ | 0.28 g |
| $KH_2PO_4$ | 0.46 g |

(*)Dye support (2) pH 7

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After a leave-in time of 30 minutes, the locks were rinsed, washed with a standard shampoo, rinsed again and then dried.

The following dyeing results were obtained.

| Examples | 6 | 7 | 8 | 9 | 10 |
|---|---|---|---|---|---|
| Shade observed | Violet-blue | Blue-violet | Violet | Red-violet | Grey |

What is claimed is:

1. A compound of formula (I), and the addition salts thereof

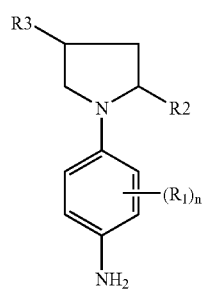

(I)

wherein:
n ranges from 0 to 4, wherein when n is greater than or equal to 2, then the radicals $R_1$ may be identical or different;
$R_1$ is chosen from halogen atoms; an onium radical Z; and $C_1$–$C_8$ aliphatic and alicyclic, saturated and unsaturated hydrocarbon-based chains, optionally comprising at least one entity chosen from oxygen, nitrogen, silicon and sulphur atoms and an $SO_2$ group, the hydrocarbon-based chains optionally being substituted with a radical chosen from hydroxyl, ($C_1$–$C_4$) oxyalkyl, amino, mono($C_1$–$C_4$)aminoalkyl, and di($C_1$–$C_4$)aminoalkyl radicals; wherein the radical $R_1$ does not comprise a peroxide bond or diazo, nitro or nitroso radicals;

$R_2$ is chosen from an onium radical Z; a carboxyl radical; a ($C_1$–$C_4$)carboxyalkyl radical; a carbamoyl radical; a ($C_1$–$C_4$)carbamoyl(alkyl) radical; a ($C_1$–$C_4$)carbamoyl (dialkyl) radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono($C_1$–$C_4$)alkylamino, di-($C_1$–$C_4$)alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_4$)alkylcarbonyl, ($C_1$–$C_4$)alkyloxycarbonyl, carbamoyl, mono($C_1$–$C_4$)alkylcarbamoyl, and di($C_1$–$C_4$)alkylcarbamoyl radicals; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and $R_3$ is chosen from an onium radical Z; a hydrogen atom; a hydroxyl radical; a ($C_1$–$C_4$)alkyloxy radical; an amino radical; a mono-($C_1$–$C_4$)alkylamino radical; a di($C_1$–$C_4$)alkylamino radical; a thiol radical; a carboxyl radical; a ($C_1$–$C_4$)alkylcarboxyl radical; a carbamoyl radical; a ($C_1$–$C_4$)alkylcarbamoyl radical; a di($C_1$–$C_4$) alkylcarbamoyl radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono-($C_1$–$C_4$)alkylamino, di($C_1$–$C_4$) alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_6$)alkylcarbonyl, ($C_1$–$C_6$)alkyloxycarbonyl, carbamoyl, mono($C_1$–$C_6$) alkylcarbamoyl, and di($C_1$–$C_6$)alkylcarbamoyl radicals, and with at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms;
wherein at least one of the groups $R_2$ and $R_3$ is chosen from an onium radical Z, wherein the onium radical Z is a nitrogen-based quaternary radical.

2. The compound according to claim 1, wherein n is equal to 0 or 1.

3. The compound according to claim 1, wherein $R_1$ is chosen from $C_1$–$C_4$ alkyl, $C_1$–$C_4$ hydroxyalkyl, $C_1$–$C_4$ aminoalkyl, $C_1$–$C_4$ alkoxy and $C_1$–$C_4$ hydroxyalkoxy radicals.

4. The compound of according to claim 3, wherein $R_1$ is chosen from methyl, hydroxymethyl, 2-hydroxyethyl, 1,2-dihydroxyethyl, methoxy, isopropyloxy and 2-hydroxyethoxy radicals.

5. The compound according to claim 1, wherein $R_2$ is an onium radical Z and $R_3$ is chosen from a hydrogen atom, a hydroxyl radical; an amino radical; an amino radical mono- or disubstituted with a radical chosen from $(C_1$–$C_6)$alkyl and $(C_1$–$C_6)$alkylcarbonyl radicals; a carbamoyl radical; and a $(C_1$–$C_6)$alkylsulphonyl radical.

6. The compound according to claim 5, wherein $R_2$ is an onium radical Z and $R_3$ is chosen from a hydrogen atom.

7. The compound according to claim 1, wherein $R_3$ is an onium radical Z and $R_2$ is chosen from a $C_1$–$C_4$ hydroxyalkyl radical, a carbamoyl radical, a mono $(C_1$–$C_4)$alkylcarbamoyl radical, a di$(C_1$–$C_4)$alkylcarbamoyl radical, a carboxyl radical, a $(C_1$–$C_4)$alkyloxycarbonyl radical, a $C_1$–$C_4$ aminoalkyl radical, and a $C_1$–$C_4$ aminoalkyl radical wherein the amine is mono- or disubstituted with a $C_1$–$C_4$ alkyl radical.

8. The compound according to claim 1, wherein $R_2$ and $R_3$ are onium radicals Z.

9. The compound according to claim 1, wherein the onium radical Z is a radical of formula (II)

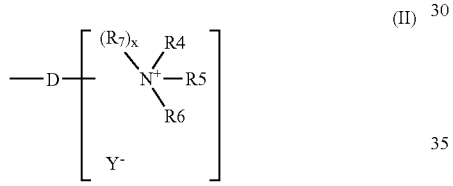

wherein:
D is a linker arm chosen from a covalent bond and linear and branched $C_1$–$C_{14}$ alkylene chains which optionally comprise at least one hetero atom chosen from oxygen, sulphur and nitrogen, are optionally substituted with at least one radical chosen from hydroxyl, $C_1$–$C_6$ alkoxy and amino radicals, and optionally comprise at least one carbonyl function;

$R_4$, $R_5$ and $R_6$, taken separately, are chosen from $C_1$–$C_{15}$ alkyl radicals; $C_1$–$C_6$ monohydroxyalkyl radicals; $C_2$–$C_6$ polyhydroxyalkyl radicals; $(C_1$–$C_6)$alkoxy-$(C_1$–$C_6)$alkyl radicals; aryl radicals; benzyl radicals; $C_1$–$C_6$ carbamoylalkyl radicals; tri$(C_1$–$C_6)$alkylsilane$(C_1$–$C_6)$alkyl radicals; $C_1$–$C_6$ aminoalkyl radicals; $C_1$–$C_6$ aminoalkyl radicals wherein the amine is mono- or disubstituted with $C_1$–$C_4$ alkyl, $(C_1$–$C_6)$alkylcarbonyl, carbamoyl or $(C_1$–$C_6)$alkylsulphonyl radicals; $C_1$–$C_6$ carboxyalkyl $(C_1$–$C_6)$alkyl radicals; $C_1$–$C_6$ carbonylalkyl $(C_1$–$C_6)$ alkyl radicals; and $C_1$–$C_6$ carbamoylalkyl $(C_1$–$C_6)$—N-alkyl radicals;

$R_4$, $R_5$ and $R_6$ together, in pairs, form, with the nitrogen atom to which they are attached a saturated 4-, 5-, 6- or 7-membered carbon-based cationic ring optionally comprising at least one hetero atom, the cationic ring optionally being substituted with a halogen atom and/or with a radical chosen from a hydroxyl radical; a $C_1$–$C_6$alkyl radical; a $C_1$–$C_6$ monohydroxyalkyl radical; a $C_2$–$C_6$ polyhydroxyalkyl radical; a $C_1$–$C_6$ alkoxy radical; a tri$(C_1$–$C_6)$alkylsilane$(C_1$–$C_6)$alkyl radical; a carbamoyl radical; a carboxyl radical; a $(C_1$–$C_6)$alkylcarbonyl radical; a thio radical; a $C_1$–$C_6$ thioalkyl radical; a $(C_1$–$C_6)$alkylthio radical; an amino radical; and an amino radical mono- or disubstituted with a radical chosen from $(C_1$–$C_6)$alkyl, $(C_1$–$C_6)$alkylcarbonyl, carbamoyl and $(C_1$–$C_6)$alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with a radical chosen from $(C_1$–$C_6)$alkyl, $(C_1$–$C_6)$alkylcarbonyl, carbamoyl and $(C_1$–$C_6)$alkylsulphonyl radicals; $C_1$–$C_6$ carboxyalkyl radicals; $C_1$–$C_6$ carbamoylalkyl radicals; $C_1$–$C_6$ trifluoroalkyl radicals; tri$(C_1$–$C_6)$alkylsilane$(C_1$–$C_6)$alkyl radicals; $C_1$–$C_6$ sulphonamido-alkyl radicals; $(C_1$–$C_6)$alkylcarboxy$(C_1$–$C_6)$alkyl radicals; $(C_1$–$C_6)$alkylsulphinyl$(C_1$–$C_6)$alkyl radicals; $(C_1$–$C_6)$alkylsulphonyl $(C_1$–$C_6)$alkyl radicals; $(C_1$–$C_6)$alkylcarbonyl$(C_1$–$C_6)$alkyl radicals; N—$(C_1$–$C_6)$alkylcarbamyl$(C_1$–$C_6)$alkyl radicals; and N—$(C_1$–$C_6)$alkylsulphonamido$(C_1$–$C_6)$alkyl radicals;

x is 0 or 1, wherein:
when x=0, then the linker arm D is attached to the nitrogen atom bearing the radicals $R_4$ to $R_6$,
when x=1, then two of the radicals $R_4$ to $R_6$ form, together with the nitrogen atom to which they are attached, a 4-, 5-, 6- or 7-membered saturated ring and the linker arm D is linked to a carbon atom of the saturated ring; and $Y^-$ is a counterion.

10. The compound according to claim 9, wherein x is equal to 0, and $R_4$, $R_5$ and $R_6$, separately, are chosen from $C_1$–$C_6$ alkyl radicals; $C_1$–$C_4$ monohydroxyalkyl radicals; $C_2$–$C_4$ polyhydroxyalkyl radicals; $(C_1$–$C_6)$alkoxy$(C_1$–$C_4)$ alkyl radicals; $C_1$–$C_6$ carbamoylalkyl radicals; and tri $(C_1$–$C_6)$alkylsilane$(C_1$–$C_6)$alkyl radicals; or $R_4$ and $R_5$ together form an azetidine, pyrrolidine, piperidine, piperazine or morpholine ring, and $R_6$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals, $C_1$–$C_6$ aminoalkyl radicals wherein the amine is mono- or disubstituted with a radical chosen from $(C_1$–$C_6)$alkyl, $(C_1$–$C_6)$alkylcarbonyl, carbamoyl and $(C_1$–$C_6)$alkylsulphonyl radicals; $C_1$–$C_6$ carbamoylalkyl radicals; tri$(C_1$–$C_6)$alkylsilane $(C_1$–$C_6)$alkyl radicals; $(C_1$–$C_6)$alkylcarboxy$(C_1$–$C_6)$alkyl radicals; $(C_1$–$C_6)$alkylcarbonyl$(C_1$–$C_6)$alkyl radicals; and N—$(C_1$–$C_6)$alkylcarbamyl$(C_1$–$C_6)$alkyl radicals.

11. The compound according to claim 9, wherein x is equal to 1 and $R_7$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with a radical chosen from $(C_1$–$C_6)$alkyl, $(C_1$–$C_6)$alkylcarbonyl, carbamoyl and $(C_1$–$C_6)$alkylsulphonyl radicals; $C_1$–$C_6$ carbamylalkyl radicals; tri$(C_1$–$C_6)$alkylsilane$(C_1$–$C_6)$alkyl radicals; $(C_1$–$C_6)$alkylcarboxy$(C_1$–$C_6)$alkyl radicals; $(C_1$–$C_6)$alkylcarbonyl$(C_1$–$C_6)$alkyl radicals; and N—$(C_1$–$C_6)$alkylcarbamoyl$(C_1$–$C_6)$alkyl radicals; $R_4$ and $R_5$ together form an azetidine, pyrrolidine, piperidine, piperazine or morpholine ring, and $R_6$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals, $C_1$–$C_6$ aminoalkyl radicals wherein the amine is mono- or disubstituted with a radical chosen from $(C_1$–$C_6)$alkyl, $(C_1$–$C_6)$alkylcarbonyl, carbamoyl and $(C_1$–$C_6)$alkylsulphonyl radicals; $C_1$–$C_6$ carbamylalkyl radicals; tri$(C_1$–$C_6)$alkylsilane($C_1$–$C_6$)alkyl radicals; ($C_1$–$C_6$)alkylcarboxy($C_1$–$C_6$) alkyl radicals; ($C_1$–$C_6$)alkylcarbonyl($C_1$–$C_6$)alkyl radicals; and N—($C_1$–$C_6$)alkylcarbamyl($C_1$–$C_6$)alkyl radicals.

12. The compound according to claim 1, wherein the onium radical Z is a trialkylammonium.

13. The compound according to claim 1, wherein D is chosen from a single bond and a $C_1$–$C_8$ alkylene chain that is optionally substituted.

14. The compound according to claim 1, wherein the onium radical Z is a radical of formula (III)

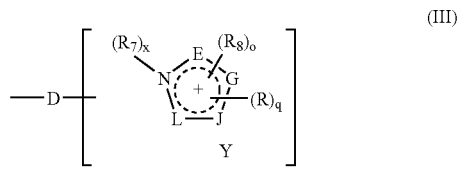

(III)

wherein:
D is a linker arm chosen from a covalent bond and linear and branched $C_1$–$C_{14}$ alkylene chains that optionally comprise at least one hetero atom chosen from oxygen, sulphur and nitrogen, are optionally substituted with at least one radical chosen from hydroxyl, $C_1$–$C_6$ alkoxy and amino radicals, and optionally comprise at least one carbonyl function;
the ring members E, G, J and L, which may be identical or different, are chosen from a carbon, oxygen, sulphur and nitrogen atoms to form a ring chosen from pyrrole, pyrazole, imidazole, triazole, oxazole, isoxazole, thiazole and isothiazole rings;
q is an integer ranging from 1 to 4;
o is an integer ranging from 1 to 3;
the sum of q+o is an integer ranging from 2 to 4;
R, which may be identical or different, is chosen from hydrogen and halogen atoms; hydroxyl radicals; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; tri($C_1$–$C_6$)alkylsilane($C_1$–$C_6$)alkyl radicals; carbamoyl radicals; carboxyl radicals; $C_1$–$C_6$ alkylcarbonyl radicals; thio radicals; $C_1$–$C_6$ thioalkyl radicals; ($C_1$–$C_6$)alkylthio radicals; amino radicals, amino radicals mono- or disubstituted with a radical chosen from ($C_1$–$C_6$)alkyl, ($C_1$–$C_6$)alkylcarbonyl, carbamoyl, and ($C_1$–$C_6$)alkylsulphonyl radicals; $C_1$–$C_6$ monohydroxyalkyl radicals; and $C_2$–$C_6$ polyhydroxyalkyl radicals; wherein the radicals R are borne by a carbon atom;
$R_8$, which may be identical or different, is chosen from a hydrogen atom; $C_1$–$C_6$ alkyl radicals; $C_1$–$C_6$ monohydroxyalkyl radicals; $C_2$–$C_6$ polyhydroxyalkyl radicals; tri($C_1$–$C_6$)alkylsilane($C_1$–$C_6$)alkyl radicals; ($C_1$–$C_6$)alkoxy($C_1$–$C_6$)alkyl radicals; $C_1$–$C_6$ carbamoylalkyl radicals; ($C_1$–$C_6$)alkylcarboxy($C_1$–$C_6$)alkyl radicals; and benzyl radicals; wherein the radicals $R_8$ are borne by a nitrogen atom;
$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is mono or di substituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$)-alkylsulphinyl($C_1$–$C_6$)alkyl radicals; ($C_1$–$C_6$)alkylsulphonyl ($C_1$–$C_6$)alkyl radicals; ($C_1$–$C_6$)alkylcarboxy($C_1$–$C_6$) alkyl radicals; N—($C_1$–$C_6$)alkylcarbamyl($C_1$–$C_6$)alkyl radicals; and N—($C_1$–$C_6$)alkylsulphonamido($C_1$–$C_6$) alkyl radicals;
x is 0 or 1, wherein:
when x=0, the linker arm D is attached to the nitrogen atom,
when x=1, the linker arm D is attached to one of the ring members E, G, J or L; and
$Y^-$ is a counterion.

15. The compound according to claim 14, wherein the ring members E, G, J and L form a pyrrole, imidazole, pyrazole, oxazole, thiazole or triazole ring.

16. The compound according to claim 15, wherein the ring members E, G, J and L form an imidazole ring.

17. The compound according to claim 14, wherein x is equal to 0 and D is chosen from a single bond and a $C_1$–$C_8$ alkylene chain optionally substituted.

18. The compound according to claim 1, wherein the onium radical Z is a radical of formula (IV)

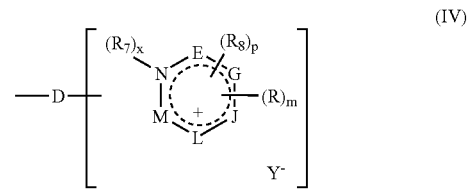

(IV)

wherein:
D is a linker arm chosen from a covalent bond and linear or branched $C_1$–$C_{14}$ alkylene chains that are optionally interrupted with at least one hetero atom chosen from oxygen, sulphur and nitrogen atoms, optionally substituted with at least one radical chosen from hydroxyl, $C_1$–$C_6$ alkoxy and amino radicals, and optionally comprise at least one carbonyl function;
the ring members E, G, J, L and M, which are identical or different, are chosen from a carbon, oxygen, sulphur and nitrogen atoms and form a ring chosen from pyridine, pyrimidine, pyrazine, triazine and pyridazine rings;
p is an integer ranging from 1 to 3;
m is an integer ranging from 1 to 5;
the sum of p+m is an integer ranging from 2 to 5;
R, which may be identical or different, is chosen from hydrogen atoms; halogen atoms; hydroxyl radicals; $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; tri($C_1$–$C_6$)alkylsilane($C_1$–$C_6$)alkyl radicals; carbamoyl radicals; carboxyl radicals; $C_1$–$C_6$ alkylcarbonyl radicals; thio radicals; $C_1$–$C_6$ thioalkyl radicals; ($C_1$–$C_6$)alkylthio radicals; amino radicals; amino radicals substituted with a radical chosen from ($C_1$–$C_6$) alkyl, ($C_1$–$C_6$)alkylcarbonyl, carbamoyl and ($C_1$–$C_6$) alkylsulphonyl radicals; $C_1$–$C_6$ monohydroxyalkyl radicals; and $C_2$–$C_6$ polyhydroxyalkyl radicals; wherein the radicals R are borne by a carbon atom;
$R_8$, which may be identical or different, is chosen from hydrogen atoms; $C_1$–$C_6$ alkyl radicals; $C_1$–$C_6$ monohydroxyalkyl radicals; $C_2$–$C_6$ polyhydroxyalkyl radicals; tri($C_1$–$C_6$)alkylsilane($C_1$–$C_6$)alkyl radicals; ($C_1$–$C_6$)alkoxy($C_1$–$C_6$)alkyl radicals; $C_1$–$C_6$ carbamylalkyl radicals; (C₁–C₆)alkylcarboxy(C₁–C₆)alkyl radicals; and benzyl radicals; wherein the radicals R₈ are borne by a nitrogen atom;

R₇ is chosen from C₁–C₆ alkyl radicals; C₁–C₆ monohydroxyalkyl radicals; C₂–C₆ polyhydroxyalkyl radicals; aryl radicals; benzyl radicals; C₁–C₆ aminoalkyl radicals; C₁–C₆ aminoalkyl radicals wherein the amine is mono- or disubstituted with a radical chosen from (C₁–C₆)alkyl, (C₁–C₆)alkylcarbonyl, carbamoyl and (C₁–C₆)alkylsulphonyl radicals; C₁–C₆ carboxyalkyl radicals; C₁–C₆ carbamoylalkyl radicals; C₁–C₆ trifluoroalkyl radicals; tri(C₁–C₆)alkylsilane(C₁–C₆)alkyl radicals; C₁–C₆ sulphonamidoalkyl radicals; (C₁–C₆) alkylcarboxy(C₁–C₆)alkyl radicals; (C₁–C₆)-alkylsulphinyl(C₁–C₆)alkyl radicals; (C₁–C₆)alkylsulphonyl (C₁–C₆)alkyl radicals; (C₁–C₆)alkylcarboxy(C₁–C₆) alkyl radicals; N—(C₁–C₆)alkylcarbamoyl(C₁–C₆) alkyl radicals; and N—(C₁–C₆)alkylsulphonamido (C₁–C₆)alkyl radicals;

x is 0 or 1, wherein:
  when x=0, the linker arm D is attached to the nitrogen atom,
  when x=1, the linker arm D is attached to one of the ring members E, G, J, L or M; and Y⁻ is a counterion.

19. The compound according to claim 18, wherein the ring members E, G, J, L and M form, together with the nitrogen of the ring, a ring chosen from pyridine and pyrimidine rings.

20. The compound according to claim 18, wherein x is equal to 0 and R is chosen from hydrogen atoms; hydroxyl radicals; C₁–C₆ alkyl radicals; C₁–C₆ monohydroxyalkyl radicals; C₂–C₆ polyhydroxyalkyl radicals; C₁–C₆ alkoxy radicals; tri(C₁–C₆)alkylsilane(C₁–C₆)alkyl radicals; carbamoyl radicals; C₁–C₆ alkylcarbonyl radicals; amino radicals; amino radicals mono- or disubstituted with a radical chosen from (C₁–C₆)alkyl, (C₁–C₆)alkylcarbonyl, carbamoyl and (C₁–C₆)alkylsulphonyl radicals; C₁–C₆ monohydroxyalkyl radicals; or C₂–C₆ polyhydroxyalkyl radicals; and R₈ is chosen from hydrogen atoms, C₁–C₆ alkyl radicals, C₁–C₆ monohydroxyalkyl radicals, C₂–C₆ polyhydroxyalkyl radicals, tri(C₁–C₆)alkylsilane(C₁–C₆)alkyl radicals, (C₁–C₆)alkoxy(C₁–C₆)alkyl radicals and C₁–C₆ carbamylalkyl radicals.

21. The compound according to claim 18, wherein x is equal to 1 and R₇ is chosen from C₁–C₆ alkyl radicals; C₁–C₆ monohydroxyalkyl radicals; C₂–C₆ polyhydroxyalkyl radicals; C₁–C₆ aminoalkyl radicals, C₁–C₆ aminoalkyl radicals wherein the amine is mono- or disubstituted with a radical chosen from (C₁–C₆)alkyl, (C₁–C₆)alkylcarbonyl, carbamoyl or (C₁–C₆)alkylsulphonyl radicals; C₁–C₆ carbamoylalkyl radicals; tri(C₁–C₆)alkylsilane(C₁–C₆)-alkyl radicals; (C₁–C₆)alkylcarbonyl(C₁–C₆)alkyl radicals; and N—(C₁–C₆)alkylcarbamyl(C₁–C₆)alkyl radicals; R is chosen from hydrogen atoms, hydroxyl radicals, C₁–C₆ alkyl radicals, C₁–C₆ monohydroxyalkyl radicals, C₂–C₆ polyhydroxyalkyl radicals, C₁–C₆ alkoxy radicals, tri(C₁–C₆)alkylsilane(C₁–C₆)alkyl radicals, carbamoyl radicals, C₁–C₆ alkylcarbonyl radicals, and amino radicals, amino radicals mono- or disubstituted with a radical chosen from (C₁–C₆) alkyl, (C₁–C₆)alkylcarbonyl, carbamoyl or (C₁–C₆)alkylsulphonyl radicals; and R₈ is chosen from hydrogen atoms, C₁–C₆ alkyl radicals, C₁–C₆ monohydroxyalkyl radicals, C₂–C₆ polyhydroxyalkyl radicals, tri(C₁–C₆)alkylsilane (C₁–C₆)alkyl radicals, (C₁–C₆)alkoxy(C₁–C₆)alkyl radicals, and C₁–C₆ carbamoylalkyl radicals.

22. The compound according to claim 18, wherein R and R₈ are chosen from hydrogen atoms and alkyl radicals that are optionally substituted and R₇ is an alkyl radical that is optionally substituted.

23. A nitrophenylene compound of formula (I')

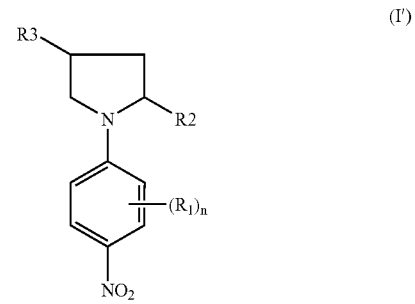

wherein:
  n ranges from 0 to 4, wherein when n is greater than or equal to 2, then the radicals R₁ may be identical or different;
  R₁ is chosen from halogen atoms; an onium radical Z; and C₁–C₈ aliphatic and alicyclic, saturated and unsaturated hydrocarbon-based chains, optionally comprising at least one entity chosen from oxygen, nitrogen, silicon and sulphur atoms and an SO₂ group, the hydrocarbon-based chains optionally being substituted with a radical chosen from hydroxyl, (C₁–C₄) oxyalkyl, amino, mono (C₁–C₄)aminoalkyl, and di(C₁–C₄)aminoalkyl radicals; wherein the radical R₁ does not comprise a peroxide bond or diazo, nitro or nitroso radicals;
  R₂ is chosen from an onium radical Z; a carboxyl radical; a (C₁–C₄)carboxyalkyl radical; a carbamoyl radical; a (C₁–C₄)carbamoyl(alkyl) radical; a (C₁–C₄)carbamoyl (dialkyl) radical; a C₁–C₆ alkyl radical; a C₁–C₆ alkyl radical, optionally unsaturated, substituted with at least one radical chosen from hydroxyl, (C₁–C₄)alkyloxy, amino, mono(C₁–C₄)alkylamino, di-(C₁–C₄)alkylamino, thiol, (C₁–C₄)alkylsulphonic and halogen radicals; a C₁–C₆ alkyl radical, optionally unsaturated, substituted with at least one radical chosen from carboxylic, (C₁–C₄)alkylcarbonyl, (C₁–C₄)alkyloxycarbonyl, carbamoyl, mono(C₁–C₄)alkylcarbamoyl, and di(C₁–C₄)alkylcarbamoyl radicals; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and
  R₃ is chosen from an onium radical Z; a hydrogen atom; a hydroxyl radical; a (C₁–C₄)alkyloxy radical; an amino radical; a mono-(C₁–C₄)alkylamino radical; a di(C₁–C₄)alkylamino radical; a thiol radical; a carboxyl radical; a (C₁–C₄)alkylcarboxyl radical; a carbamoyl radical; a (C₁–C₄)alkylcarbamoyl radical; a di(C₁–C₄) alkylcarbamoyl radical; a C₁–C₆ alkyl radical; a C₁–C₆ alkyl radical, optionally unsaturated, substituted with at least one radical chosen from hydroxyl, (C₁–C₄)alkyloxy, amino, mono-(C₁–C₄)alkylamino, di(C₁–C₄) alkylamino, thiol, (C₁–C₄)alkylsulphonic and halogen radicals; a C₁–C₆ alkyl radical, optionally unsaturated, substituted with at least one radical chosen from carboxylic, (C₁–C₆)alkylcarbonyl, (C₁–C₆)alkyloxycarbonyl, carbamoyl, mono(C₁–C₆) alkylcarbamoyl, and di(C₁–C₆)alkylcarbamoyl radicals, and with at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms;

wherein at least one of the groups $R_2$ and $R_3$ is chosen from an onium radical Z, wherein the onium radical Z is a nitrogen-based quaternary radical.

24. A dye composition comprising at least one oxidation base chosen from compounds of formula (I), and the addition salts thereof

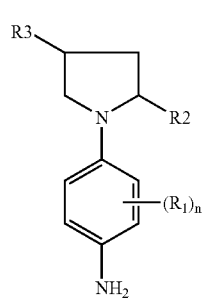

(I)

wherein:
n ranges from 0 to 4, wherein when n is greater than or equal to 2, then the radicals $R_1$ may be identical or different;

$R_1$ is chosen from halogen atoms; an onium radical Z; and $C_1$–$C_8$ aliphatic and alicyclic, saturated and unsaturated hydrocarbon-based chains, optionally comprising at least one entity chosen from oxygen, nitrogen, silicon and sulphur atoms and an $SO_2$ group, the hydrocarbon-based chains optionally being substituted with a radical chosen from hydroxyl, ($C_1$–$C_4$) oxyalkyl, amino, mono ($C_1$–$C_4$)aminoalkyl, and di($C_1$–$C_4$)aminoalkyl radicals; wherein the radical $R_1$ does not comprise a peroxide bond or diazo, nitro or nitroso radicals;

$R_2$ is chosen from an onium radical Z; a carboxyl radical; a ($C_1$–$C_4$)carboxyalkyl radical; a carbamoyl radical; a ($C_1$–$C_4$)carbamoyl(alkyl) radical; a ($C_1$–$C_4$)carbamoyl (dialkyl) radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono($C_1$–$C_4$)alkylamino, di-($C_1$–$C_4$)alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_4$)alkylcarbonyl, ($C_1$–$C_4$)alkyloxycarbonyl, carbamoyl, mono($C_1$–$C_4$)alkylcarbamoyl, and di($C_1$–$C_4$)alkylcarbamoyl radicals; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and $R_3$ is chosen from an onium radical Z; a hydrogen atom; a hydroxyl radical; a ($C_1$–$C_4$)alkyloxy radical; an amino radical; a mono-($C_1$–$C_4$)alkylamino radical; a di($C_1$–$C_4$)alkylamino radical; a thiol radical; a carboxyl radical; a ($C_1$–$C_4$)alkylcarboxyl radical; a carbamoyl radical; a ($C_1$–$C_4$)alkylcarbamoyl radical; a di($C_1$–$C_4$) alkylcarbamoyl radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono-($C_1$–$C_4$)alkylamino, di($C_1$–$C_4$) alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_6$)alkylcarbonyl, ($C_1$–$C_6$)alkyloxycarbonyl, carbamoyl, mono($C_1$–$C_6$) alkylcarbamoyl, and di($C_1$–$C_6$)alkylcarbamoyl radicals, and with at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms;

wherein at least one of the groups $R_2$ and $R_3$ is chosen from an onium radical Z, wherein the onium radical Z is a nitrogen-based quaternary radical.

25. The composition according to claim 24, further comprising at least one coupler chosen from meta-phenylenediamines, meta-aminophenols, meta-diphenols, naphthalenic couplers and heterocyclic couplers, and the addition salts thereof.

26. The composition according to claim 24, further comprising at least one additional oxidation base other than the oxidation bases of formula (I), chosen from para-phenylenediamines, bis(phenyl)alkylenediamines, para-aminophenols, ortho-aminophenols and heterocyclic bases, and the addition salts thereof.

27. The composition according to claim 26, wherein for the at least one compound of formula (I) and for the at least one additional oxidation base, if present, each oxidation base in the dye composition is present in an amount ranging from about 0.001% to about 10% by weight, relative to the total weight of the dye composition.

28. The composition according to claim 26, wherein for the at least one compound of formula (I) and for the at least one additional oxidation base, if present, each oxidation base in the dye composition is present in an amount ranging from about 0.005% to about 6% by weight, relative to the total weight of the dye composition.

29. The composition according to claim 25, wherein the at least one coupler is present in the dye composition in an amount ranging from about 0.001% to about 10% by weight, relative to the total weight of the dye composition.

30. The composition according to claim 25, wherein the at least one coupler is present in the dye composition in an amount ranging from about 0.005% to about 6% by weight, relative to the total weight of the dye composition.

31. The composition according to claim 24, further comprising a cosmetic medium suitable for dyeing human keratin fibers.

32. A process for oxidation dyeing of keratin fibers comprising applying to the fibers, in the presence of an oxidizing agent for a time sufficient to develop a desired coloration, a dye composition comprising at least one oxidation base chosen from compounds of formula (I), and the addition salts thereof

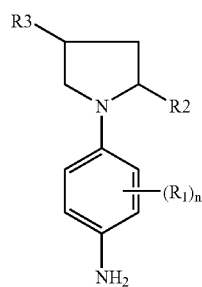

wherein:
- n ranges from 0 to 4, wherein when n is greater than or equal to 2, then the radicals $R_1$ may be identical or different;
- $R_1$ is chosen from halogen atoms; an onium radical Z; and $C_1$–$C_8$ aliphatic and alicyclic, saturated and unsaturated hydrocarbon-based chains, optionally comprising at least one entity chosen from oxygen, nitrogen, silicon and sulphur atoms and an $SO_2$ group, the hydrocarbon-based chains optionally being substituted with a radical chosen from hydroxyl, ($C_1$–$C_4$) oxyalkyl, amino, mono($C_1$–$C_4$)aminoalkyl, and di($C_1$–$C_4$)aminoalkyl radicals; wherein the radical $R_1$ does not comprise a peroxide bond or diazo, nitro or nitroso radicals;
- $R_2$ is chosen from an onium radical Z; a carboxyl radical; a ($C_1$–$C_4$)carboxyalkyl radical; a carbamoyl radical; a ($C_1$–$C_4$)carbamoyl(alkyl) radical; a ($C_1$–$C_4$)carbamoyl (dialkyl) radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono($C_1$–$C_4$)alkylamino, di-($C_1$–$C_4$)alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_4$)alkylcarbonyl, ($C_1$–$C_4$)alkyloxycarbonyl, carbamoyl, mono($C_1$–$C_4$)alkylcarbamoyl, and di($C_1$–$C_4$)alkylcarbamoyl radicals; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and
- $R_3$ is chosen from an onium radical Z; a hydrogen atom; a hydroxyl radical; a ($C_1$–$C_4$)alkyloxy radical; an amino radical; a mono-($C_1$–$C_4$)alkylamino radical; a di($C_1$–$C_4$)alkylamino radical; a thiol radical; a carboxyl radical; a ($C_1$–$C_4$)alkylcarboxyl radical; a carbamoyl radical; a ($C_1$–$C_4$)alkylcarbamoyl radical; a di($C_1$–$C_4$) alkylcarbamoyl radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono-($C_1$–$C_4$)alkylamino, di($C_1$–$C_4$) alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_6$)alkylcarbonyl, ($C_1$–$C_6$)alkyloxycarbonyl, carbamoyl, mono($C_1$–$C_6$) alkylcarbamoyl, and di($C_1$–$C_6$)alkylcarbamoyl radicals, and with at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms;
- wherein at least one of the groups $R_2$ and $R_3$ is chosen from an onium radical Z, wherein the onium radical Z is a nitrogen-based quaternary radical.

33. The process according to claim 32, wherein the at least one oxidizing agent is chosen from hydrogen peroxide, urea peroxide, alkali metal bromates, persalts, peracids and oxidase enzymes.

34. A multi-compartment kit comprising a first compartment comprising at least one dye composition, the dye composition comprising at least one oxidation base chosen from compounds of formula (I), and the addition salts thereof

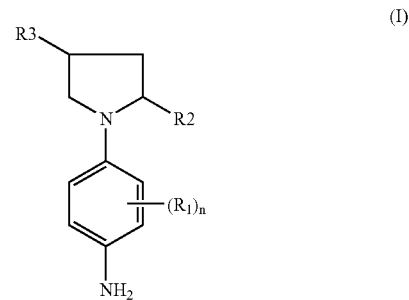

wherein:
- n ranges from 0 to 4, wherein when n is greater than or equal to 2, then the radicals $R_1$ may be identical or different;
- $R_1$ is chosen from halogen atoms; an onium radical Z; and $C_1$–$C_8$ aliphatic and alicyclic, saturated and unsaturated hydrocarbon-based chains, optionally comprising at least one entity chosen from oxygen, nitrogen, silicon and sulphur atoms and an $SO_2$ group, the hydrocarbon-based chains optionally being substituted with a radical chosen from hydroxyl, ($C_1$–$C_4$) oxyalkyl, amino, mono ($C_1$–$C_4$)aminoalkyl, and di($C_1$–$C_4$)aminoalkyl radicals; wherein the radical $R_1$ does not comprise a peroxide bond or diazo, nitro or nitroso radicals;
- $R_2$ is chosen from an onium radical Z; a carboxyl radical; a ($C_1$–$C_4$)carboxyalkyl radical; a carbamoyl radical; a ($C_1$–$C_4$)carbamoyl(alkyl) radical; a ($C_1$–$C_4$)carbamoyl (dialkyl) radical; a $C_1$–$C_6$ alkyl radical; a $C_1$–$C_6$ alkyl radical, optionally unsaturated, substituted with at least one radical chosen from hydroxyl, ($C_1$–$C_4$)alkyloxy, amino, mono($C_1$–$C_4$)alkylamino, di-($C_1$–$C_4$)alkylamino, thiol, ($C_1$–$C_4$)alkylsulphonic and halogen radicals; a $C_1$–$C_6$ alkyl radical, optionally unsaturated, substituted with at least one radical chosen from carboxylic, ($C_1$–$C_4$)alkylcarbonyl, ($C_1$–$C_4$)alkyloxycarbonyl, carbamoyl, mono($C_1$–$C_4$)alkylcarbamoyl, and di($C_1$–$C_4$)alkylcarbamoyl radicals; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and
- $R_3$ is chosen from an onium radical Z; a hydrogen atom; a hydroxyl radical; a ($C_1$–$C_4$)alkyloxy radical; an amino radical; a mono-($C_1$–$C_4$)alkylamino radical; a di($C_1$–$C_4$)alkylamino radical; a thiol radical; a carboxyl radical; a ($C_1$–$C_4$)alkylcarboxyl radical; a carbamoyl radical; a $(C_1-C_4)$alkylcarbamoyl radical; a di$(C_1-C_4)$ alkylcarbamoyl radical; a $C_1-C_6$ alkyl radical; a $C_1-C_6$ alkyl radical, optionally unsaturated, substituted with at least one radical chosen from hydroxyl, $(C_1-C_4)$alkyloxy, amino, mono-$(C_1-C_4)$alkylamino, di$(C_1-C_4)$ alkylamino, thiol, $(C_1-C_4)$alkylsulphonic and halogen radicals; a $C_1-C_6$ alkyl radical, optionally unsaturated, substituted with at least one radical chosen from carboxylic, $(C_1-C_6)$alkylcarbonyl, $(C_1-C_6)$alkyloxycarbonyl, carbamoyl, mono$(C_1-C_6)$ alkylcarbamoyl, and di$(C_1-C_6)$alkylcarbamoyl radicals, and with at least one heterocycle, wherein said at least one heterocycle is saturated or unsaturated, is chosen from nitrogen-containing, oxygen-containing and sulphur-containing heterocycles, and comprises at least 4, 5, 6 or 7 atoms; and at least one heterocycle, wherein said at least one heterocycle is saturated or unsaturated, is chosen from nitrogen-containing, oxygen-containing and sulphur-containing heterocycles, and comprises at least 4, 5, 6 or 7 atoms;

wherein at least one of the groups $R_2$ and $R_3$ is chosen from an onium radical Z, wherein the onium radical Z is a nitrogen-based quaternary radical; and a second compartment comprising at least one oxidizing agent.

\* \* \* \* \*